US010111962B2

(12) United States Patent
Leger et al.

(10) Patent No.: US 10,111,962 B2
(45) Date of Patent: Oct. 30, 2018

(54) PEPTIDE-LINKED MORPHOLINO ANTISENSE OLIGONUCLEOTIDES FOR TREATMENT OF MYOTONIC DYSTROPHY

(71) Applicant: Genzyme Corporation, Cambridge, MA (US)

(72) Inventors: Andrew Leger, Boston, MA (US); Bruce Wentworth, Northborough, MA (US); Carol A. Nelson, Westford, MA (US); Timothy E. Weeden, Sturbridge, MA (US); Nicholas Clayton, Sudbury, MA (US); Seng Cheng, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/431,115

(22) PCT Filed: Sep. 24, 2013

(86) PCT No.: PCT/US2013/061320
§ 371 (c)(1),
(2) Date: Mar. 25, 2015

(87) PCT Pub. No.: WO2014/052276
PCT Pub. Date: Apr. 3, 2014

(65) Prior Publication Data
US 2015/0238627 A1  Aug. 27, 2015

Related U.S. Application Data

(60) Provisional application No. 61/705,335, filed on Sep. 25, 2012.

(51) Int. Cl.
*A61K 48/00* (2006.01)
*A61K 47/48* (2006.01)
*C12N 15/113* (2010.01)
*A61K 31/712* (2006.01)

(52) U.S. Cl.
CPC ...... *A61K 47/48246* (2013.01); *A61K 31/712* (2013.01); *C12N 15/113* (2013.01); *C12N 2310/11* (2013.01); *C12N 2310/3233* (2013.01); *C12N 2310/3513* (2013.01); *C12N 2320/32* (2013.01)

(58) Field of Classification Search
CPC ...................................................... A61K 48/00
See application file for complete search history.

(56) References Cited

U.S. PATENT DOCUMENTS

| 4,458,066 | A | 7/1984 | Caruthers et al. |
| 5,034,506 | A | 7/1991 | Summerton et al. |
| 5,142,047 | A | 8/1992 | Summerton et al. |
| 5,166,315 | A | 11/1992 | Summerton et al. |
| 5,185,444 | A | 2/1993 | Summerton et al. |
| 5,217,866 | A | 6/1993 | Summerton et al. |
| 5,436,221 | A | 7/1995 | Kitaguchi et al. |
| 5,506,337 | A | 4/1996 | Summerton et al. |
| 5,521,063 | A | 5/1996 | Summerton et al. |
| 5,698,685 | A | 12/1997 | Summerton et al. |
| 8,741,863 | B2 * | 6/2014 | Moulton ............ C12N 15/87 514/44 A |
| 8,835,402 | B2 * | 9/2014 | Kole ................ C12N 15/87 514/44 A |
| 2009/0099066 | A1 | 4/2009 | Moulton et al. |
| 2009/0286693 | A1 | 11/2009 | Chang et al. |
| 2011/0171184 | A1 | 7/2011 | Hovig et al. |
| 2011/0269665 | A1 | 11/2011 | Kole |
| 2012/0058946 | A1 | 3/2012 | Moulton et al. |
| 2015/0080311 | A1 | 3/2015 | Moulton et al. |

FOREIGN PATENT DOCUMENTS

| EP | 0335423 A2 | 10/1989 |
| JP | H01-316400 A | 12/1989 |
| JP | H05-186499 A | 7/1993 |
| JP | 2010-532168 A | 10/2010 |
| RU | 2435859 C2 | 12/2011 |
| WO | 2008036127 A2 | 3/2008 |
| WO | WO-2010/037539 A1 | 4/2010 |
| WO | WO-2013/082548 A1 | 6/2013 |

OTHER PUBLICATIONS

Abes., et al., "Vectorization of Morpholino Oligomers by the (R-Ahx-r)4 Peptide Allows Efficient Splicing Correction in the Absence of Endosomolytic Agents," Journal of Controlled Release, 2006, vol. 116 (3), pp. 304-313.
Adams., "Hindered Dialkylamino Nucleoside Phosphite Reagents in the Synthesis of Two DNA 51-Mers", Journal of the American Chemical Society, 1983, vol. 105, p. 661.
Beaucage, S.L., et al. "Deoxynucleoside Phosphoramidites—a New Class of Key Intermediates for Deoxypolynucleotide Synthesis," Tetrahedron Letters, 1981, vol. 22, pp. 1859-1862 (Exhibit 19).
Belousov E.S., et al., "Sequence-specific Targeting and Covalent Modification of Human Genomic DNA," Nucleic Acids Research, 1997, vol. 25 (17), pp. 3440-3444.
Blommers M.J., et al., "Effects of the Introduction of L-nucleotides into DNA. Solution Structure of the Heterochiral Duplex D(G-c-g-(L)t-g-c-g).d(C-g-c-a-c-g-c) Studied by NMR Spectroscopy," Biochemistry, 1994, vol. 33 (25), pp. 7886-7896.
Brown E.L., et al., "Chemical Synthesis and Cloning of a Tyrosine TRNA Gene," Methods in Enzymology, 1979, vol. 68, pp. 109-151.
Caruthers M.H., et al., "Chemical Synthesis and Biological Studies on Mutated Gene-control Regions ," Cold Spring Harbor Symposia on Quantitative Biology, 1982, vol. 47, pp. 411-418.

(Continued)

*Primary Examiner* — Kimberly Chong
(74) *Attorney, Agent, or Firm* — Morrison & Foerster LLP

(57) ABSTRACT

Provided herein are peptide-linked morpholino (PPMO) antisense oligonucleotides that target the poly CUG repeat tract in the 3' untranslated region of the gene encoding dystrophia myotonica-protein kinase (DMPK) and methods for systemic administration of the same for the treatment of mytonic dystrophy type I (DM1).

21 Claims, 6 Drawing Sheets

Specification includes a Sequence Listing.

(56) References Cited

OTHER PUBLICATIONS

Day J.W., et al., "RNA Pathogenesis of the Myotonic Dystrophies," Neuromuscul Disorder, 2005, vol. 15 (1), pp. 5-16.
Faustino N.A., et al., "Pre-MRNA Splicing and Human Disease," Genes & Development, 2003, vol. 17 (4), pp. 419-437.
Frenkel K., et al., "7,12-dimethylbenz[a]anthracene Induces Oxidative DNA Modification in Vivo," Free Radical Biology & Medicine, 1995, vol. 19 (3), pp. 373-380.
International Preliminary Report on Patentability for Application No. PCT/US2013/061320, dated Mar. 31, 2015, 7 pages.
International Search Report and Written Opinion for Application No. PCT/US2013/061320, dated Jan. 30, 2014, 11 pages.
Jiang H., et al., "Myotonic Dystrophy Type 1 Is Associated with Nuclear Foci of Mutant RNA, Sequestration of Muscleblind Proteins and Deregulated Alternative Splicing in Neurons," Human Molecular Genetics, 2004, vol. 13 (24), pp. 3079-3088.
Kuyumcu-Martinez N.M., et al., "Increased Steady-state Levels of CUGBP1 in Myotonic Dystrophy 1 are Due to PKC-mediated Hyperphosphorylation," Molecular Cell, 2007, vol. 28 (1), pp. 68-78.
Lee J.E., et al., "RNase H-mediated Degradation of Toxic RNA in Myotonic Dystrophy Type 1," Proceedings of the National Academy of Sciences of the United States of America, 2012, vol. 109 (11), pp. 4221-4226.
Leger A.J., et al, , "Systemic Delivery of a Peptide-linked Morpholino Oligonucleotide Neutralizes Mutant Rna Toxicity in a Mouse Model of Myotonic Dystrophy," Nucleic Acid Therapeutics, 2013, vol. 23 (2), pp. 109-117.
Lin X., et al., "Failure of MBNI1-dependent Post-Natal Splicing Transitions in Myotonic Dystrophy," Human Molecular Genetics, 2006, vol. 15 (13), pp. 2087-2097.
Logigian E.L., et al., "Mexiletine is an Effective Antimyotonia Treatment in Myotonic Dystrophy Type 1," Neurology, 2010, vol. 74 (18), pp. 1441-1448.
Magana J.J., et al., "Perspectives on Gene Therapy in Myotonic Dystrophy Type 1," Journal of Neuroscience Research, 2011, vol. 89 (3), pp. 275-285.
Mankodi A., et al., "Expanded Cug Repeats Trigger Aberrant Splicing of CLC-1 Chloride Channel Pre-MRNA and Hyperexcitability of Skeletal Muscle in Myotonic Dystrophy," Molecular Cell, 2002, vol. 10 (1), pp. 35-44.
Mankodi A., et al., "Muscleblind Localizes to Nuclear Foci of Aberrant RNA in Myotonic Dystrophy Types 1 and 2," Human Molecular Genetics, 2001, vol. 10 (19), pp. 2165-2170.
Mankodi A., et al., "Myotonic Dystrophy in Transgenic Mice Expressing an Expanded Cug Repeat," Science, 2000, vol. 289 (5485), pp. 1769-1773.
Mankodi A., et al., "Ribonuclear Inclusions in Skeletal Muscle in Myotonic Dystrophy Types 1 and 2," Annals of Neurology, 2003, vol. 54 (6), pp. 760-768.
Miller J.W., et al., "Recruitment of Human Muscleblind Proteins to (CUG)(N) Expansions Associated with Myotonic Dystrophy," The Embo Journal, 2000, vol. 19 (17), pp. 4439-4448.
Mulders S.A., et al., "Triplet-repeat Oligonucleotide-mediated Reversal of RNA Toxicity in Myotonic Dystrophy," Proceedings of the National Academy of Sciences of the United States of America, 2009, vol. 106 (33), pp. 13915-13920.
Mykowska A., et al., "Cag Repeats Mimic Cug Repeats in the Misregulation of Alternative Splicing," Nucleic Acids Research, 2011, vol. 39 (20), pp. 8938-8951.
Narang S.A., et al., "Improved Phosphotriester Method for the Synthesis of Gene Fragments," Methods in Enzymology, 1979, vol. 68, pp. 90-98.
Ofori L.O., et al., "From Dynamic Combinatorial 'hit' to Lead: in Vitro and in Vivo Activity of Compounds Targeting the Pathogenic RNAs that Cause Myotonic Dystrophy," Nucleic Acids Research, 2012, vol. 40 (13), pp. 6380-6390.
Osborne R.J., et al., "Rna-dominant Diseases," Human Molecular Genetics, 2006, vol. 15SpecNo2, pp. R162-R169.
Osborne R.J., et al., "Transcriptional and Post-transcriptional Impact of Toxic RNA in Myotonic Dystrophy," Human Molecular Genetics, 2009, vol. 18 (8), pp. 1471-1481.
Parkesh R., et al., "Design of a Bioactive Small Molecule that Targets the Myotonic Dystrophy Type 1 RNA via an RNA Motif-ligand Database and Chemical Similarity Searching," Journal of the American Chemical Society, 2012, vol. 134 (10), pp. 4731-4742.
Philips A.V., et al., "Disruption of Splicing Regulated by a CUG-binding Protein in Myotonic Dystrophy," Science, 1998, vol. 280, pp. 737-741.
Sazani P., et al., "Systemically Delivered Antisense Oligomers Upregulate Gene Expression in Mouse Tissues," Nature Biotechnology, 2002, vol. 20 (12), pp. 1228-1233.
Taneja K.L., et al., "Foci of Trinucleotide Repeat Transcripts in Nuclei of Myotonic Dystrophy Cells and Tissues," The Journal of Cell Biology, 1995, vol. 128 (6), pp. 995-1002.
Timchenko L.T., et al., "Identification of a (CUG)n Triplet Repeat RNA-binding Protein and its Expression in Myotonic Dystrophy," Nucleic Acids Research, 1996, vol. 24 (22), pp. 4407-4414.
Timchenko N.A., et al., "RNA CUG Repeats Sequester CUGBP1 and Alter Protein Levels and Activity of CUGBP1," The Journal of Biological Chemistry, 2001, vol. 276 (11), pp. 7820-7826.
Turner C., et al., "The Myotonic Dystrophies: Diagnosis and Management," Journal of Neurology, Neurosurgery & Psychiatry, 2010, vol. 81 (4), pp. 358-367.
Warf M.B., et al., "Pentamidine Reverses the Splicing Defects Associated with Myotonic Dystrophy," Proceedings of the National Academy of Sciences of the United States of America, 2009, vol. 106 (44), pp. 18551-18556.
Wheeler T.M., et al., "Correction of CLC-1 Splicing Eliminates Chloride Channelopathy and Myotonia in Mouse Models of Myotonic Dystrophy," The Journal of Clinical Investigation, 2007, vol. 117 (12), pp. 3952-3957.
Wheeler T.M., et al., "Myotonic Dystrophy: RNA-mediated Muscle Disease," Current Opinion in Neurology, 2007, vol. 20 (5), pp. 572-576.
Wheeler T.M., et al., "Reversal of RNA Dominance by Displacement of Protein Sequestered on Triplet Repeat RNA," Science, 2009, vol. 325, pp. 336-339.
Wheeler T.M., et al., "Targeting Nuclear RNA for in Vivo Correction of Myotonic Dystrophy," Nature, 2012, vol. 488 (7409), pp. 111-115.

* cited by examiner a b

SEQUENCE LISTING

```
<160> NUMBER OF SEQ ID NOS: 17

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Gly or Ala
<220> FEATURE:
<221> NAME/KEY: MISC_FEATURE
<222> LOCATION: (6)..(7)
<223> OTHER INFORMATION: May or may not be present
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (13)..(18)
<223> OTHER INFORMATION: Gly or Ala
<220> FEATURE:
<221> NAME/KEY: MISC_FEATURE
<222> LOCATION: (17)..(18)
<223> OTHER INFORMATION: May or may not be present
<220> FEATURE:
<221> NAME/KEY: MOD_RES
<222> LOCATION: (21)..(21)
<223> OTHER INFORMATION: Beta-Ala
<220> FEATURE:
<221> NAME/KEY: MOD_RES
<222> LOCATION: (23)..(28)
<223> OTHER INFORMATION: Gly or Ala
<220> FEATURE:
<221> NAME/KEY: MISC_FEATURE
<222> LOCATION: (27)..(28)
<223> OTHER INFORMATION: May or may not be present
<220> FEATURE:
<221> NAME/KEY: MOD_RES
<222> LOCATION: (29)..(29)
<223> OTHER INFORMATION: Beta-Ala
<220> FEATURE:
<223> OTHER INFORMATION: See specification as filed for detailed
      description of substitutions and preferred embodiments

<400> SEQUENCE: 1

Arg Xaa Xaa Xaa Xaa Xaa Xaa Arg Arg Ala Arg Arg Xaa Xaa Xaa Xaa
1               5                   10                  15

Xaa Xaa Arg Arg Ala Arg Xaa Xaa Xaa Xaa Xaa Xaa Ala
            20                  25
```

```
<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(7)
<223> OTHER INFORMATION: Gly or Ala
<220> FEATURE:
<221> NAME/KEY: MISC_FEATURE
<222> LOCATION: (6)..(7)
<223> OTHER INFORMATION: May or may not be present
<220> FEATURE:
<221> NAME/KEY: MOD_RES
<222> LOCATION: (10)..(15)
<223> OTHER INFORMATION: Gly or Ala
<220> FEATURE:
<221> NAME/KEY: MISC_FEATURE
<222> LOCATION: (14)..(15)
<223> OTHER INFORMATION: May or may not be present
<220> FEATURE:
<221> NAME/KEY: MOD_RES
<222> LOCATION: (18)..(23)
<223> OTHER INFORMATION: Gly or Ala
<220> FEATURE:
<221> NAME/KEY: MISC_FEATURE
<222> LOCATION: (22)..(23)
<223> OTHER INFORMATION: May or may not be present
<220> FEATURE:
<221> NAME/KEY: MOD_RES
<222> LOCATION: (26)..(31)
<223> OTHER INFORMATION: Gly or Ala
<220> FEATURE:
<221> NAME/KEY: MISC_FEATURE
<222> LOCATION: (30)..(31)
<223> OTHER INFORMATION: May or may not be present
<220> FEATURE:
<221> NAME/KEY: MOD_RES
<222> LOCATION: (33)..(38)
<223> OTHER INFORMATION: Gly or Ala
<220> FEATURE:
<221> NAME/KEY: MISC_FEATURE
<222> LOCATION: (37)..(38)
<223> OTHER INFORMATION: May or may not be present
<220> FEATURE:
<221> NAME/KEY: MOD_RES
<222> LOCATION: (39)..(39)
<223> OTHER INFORMATION: Beta-Ala
<220> FEATURE:
<223> OTHER INFORMATION: See specification as filed for detailed
      description of substitutions and preferred embodiments

<400> SEQUENCE: 2

Arg Xaa Xaa Xaa Xaa Xaa Xaa Arg Arg Xaa Xaa Xaa Xaa Xaa Xaa Arg
1               5                   10                  15

Arg Xaa Xaa Xaa Xaa Xaa Xaa Arg Arg Xaa Xaa Xaa Xaa Xaa Xaa Arg
                20                  25                  30

Xaa Xaa Xaa Xaa Xaa Xaa Ala
        35

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Synthetic
      morpholino oligonucleotide
<220> FEATURE:
<221> NAME/KEY: modified_base
<222> LOCATION: (1)..(75)
<223> OTHER INFORMATION: Phosphorodiamidate morpholino nucleotide
<220> FEATURE:
```

```
<221> NAME/KEY: misc_feature
<222> LOCATION: (1)..(75)
<223> OTHER INFORMATION: This sequence may encompass 5-25 'AGC'
      repeating units, wherein some positions may be absent

<400> SEQUENCE: 3
agcagcagca gcagcagcag cagcagcagc agcagcagca gcagcagcag cagcagcagc      60
agcagcagca gcagc                                                      75

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Synthetic
      morpholino oligonucleotide
<220> FEATURE:
<221> NAME/KEY: modified_base
<222> LOCATION: (1)..(75)
<223> OTHER INFORMATION: Phosphorodiamidate morpholino nucleotide
<220> FEATURE:
<221> NAME/KEY: misc_feature
<222> LOCATION: (1)..(75)
<223> OTHER INFORMATION: This sequence may encompass 5-25 'GCA'
      repeating units, wherein some positions may be absent

<400> SEQUENCE: 4
gcagcagcag cagcagcagc agcagcagca gcagcagcag cagcagcagc agcagcagca      60
gcagcagcag cagca                                                      75

<210> SEQ ID NO 5
<211> LENGTH: 75
<212> TYPE: DNA
<213> ORGANISM: Artificial Sequence
<220> FEATURE:
<223> OTHER INFORMATION: Description of Artificial Sequence: Synthetic
      morpholino oligonucleotide
<220> FEATURE:
<221> NAME/KEY: modified_base
<222> LOCATION: (1)..(75)
<223> OTHER INFORMATION: Phosphorodiamidate morpholino nucleotide
<220> FEATURE:
<221> NAME/KEY: misc_feature
<222> LOCATION: (1)..(75)
<223> OTHER INFORMATION: This sequence may encompass 5-25 'CAG'
      repeating units, wherein some positions may be absent

<400> SEQUENCE: 5
cagcagcagc agcagcagca gcagcagcag cagcagcagc agcagcagca gcagcagcag      60
cagcagcagc agcag                                                      75

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agcagcagca gcagcagcag cagca                                           25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 7
gcagcagcag cagcagcagc                                                    20

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or D-Arg
<220> FEATURE:
<221> NAME/KEY: MOD_RES
<222> LOCATION: (2)..(7)
<223> OTHER INFORMATION: Gly or Ala
<220> FEATURE:
<221> NAME/KEY: MISC_FEATURE
<222> LOCATION: (6)..(7)
<223> OTHER INFORMATION: May or may not be present
<220> FEATURE:
<221> NAME/KEY: MOD_RES
<222> LOCATION: (8)..(9)
<223> OTHER INFORMATION: Arg or D-Arg
<220> FEATURE:
<221> NAME/KEY: MOD_RES
<222> LOCATION: (10)..(10)
<223> OTHER INFORMATION: Beta-Ala
<220> FEATURE:
<221> NAME/KEY: MOD_RES
<222> LOCATION: (11)..(12)
<223> OTHER INFORMATION: Arg or D-Arg
<220> FEATURE:
<221> NAME/KEY: MOD_RES
<222> LOCATION: (13)..(18)
<223> OTHER INFORMATION: Gly or Ala
<220> FEATURE:
<221> NAME/KEY: MISC_FEATURE
<222> LOCATION: (17)..(18)
<223> OTHER INFORMATION: May or may not be present
<220> FEATURE:
<221> NAME/KEY: MOD_RES
<222> LOCATION: (19)..(20)
<223> OTHER INFORMATION: Arg or D-Arg
<220> FEATURE:
<221> NAME/KEY: MOD_RES
<222> LOCATION: (21)..(21)
<223> OTHER INFORMATION: Beta-Ala
<220> FEATURE:
<221> NAME/KEY: MOD_RES
<222> LOCATION: (22)..(22)
<223> OTHER INFORMATION: Arg or D-Arg
<220> FEATURE:
<221> NAME/KEY: MOD_RES
<222> LOCATION: (23)..(28)
<223> OTHER INFORMATION: Gly or Ala
<220> FEATURE:
<221> NAME/KEY: MISC_FEATURE
<222> LOCATION: (27)..(28)
<223> OTHER INFORMATION: May or may not be present
<220> FEATURE:
<221> NAME/KEY: MOD_RES
<222> LOCATION: (29)..(29)
<223> OTHER INFORMATION: Beta-Ala
<220> FEATURE:
<223> OTHER INFORMATION: See specification as filed for detailed
      description of substitutions and preferred embodiments

<400> SEQUENCE: 8

Arg Xaa Xaa Xaa Xaa Xaa Xaa Arg Arg Ala Arg Arg Xaa Xaa Xaa Xaa
1               5                   10                  15

Xaa Xaa Arg Arg Ala Arg Xaa Xaa Xaa Xaa Xaa Xaa Ala
            20                  25

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Arg or D-Arg
<220> FEATURE:
<221> NAME/KEY: MOD_RES
<222> LOCATION: (2)..(7)
<223> OTHER INFORMATION: Gly or Ala
<220> FEATURE:
<221> NAME/KEY: MISC_FEATURE
<222> LOCATION: (6)..(7)
<223> OTHER INFORMATION: May or may not be present
<220> FEATURE:
<221> NAME/KEY: MOD_RES
<222> LOCATION: (8)..(9)
<223> OTHER INFORMATION: Arg or D-Arg
<220> FEATURE:
<221> NAME/KEY: MOD_RES
<222> LOCATION: (10)..(15)
<223> OTHER INFORMATION: Gly or Ala
<220> FEATURE:
<221> NAME/KEY: MISC_FEATURE
<222> LOCATION: (14)..(15)
<223> OTHER INFORMATION: May or may not be present
<220> FEATURE:
<221> NAME/KEY: MOD_RES
<222> LOCATION: (16)..(17)
<223> OTHER INFORMATION: Arg or D-Arg
<220> FEATURE:
<221> NAME/KEY: MOD_RES
<222> LOCATION: (18)..(23)
<223> OTHER INFORMATION: Gly or Ala
<220> FEATURE:
<221> NAME/KEY: MISC_FEATURE
<222> LOCATION: (22)..(23)
<223> OTHER INFORMATION: May or may not be present
<220> FEATURE:
<221> NAME/KEY: MOD_RES
<222> LOCATION: (24)..(25)
<223> OTHER INFORMATION: Arg or D-Arg
<220> FEATURE:
<221> NAME/KEY: MOD_RES
<222> LOCATION: (26)..(31)
<223> OTHER INFORMATION: Gly or Ala
<220> FEATURE:
<221> NAME/KEY: MISC_FEATURE
<222> LOCATION: (30)..(31)
<223> OTHER INFORMATION: May or may not be present
<220> FEATURE:
<221> NAME/KEY: MOD_RES
<222> LOCATION: (32)..(32)
<223> OTHER INFORMATION: Arg or D-Arg
<220> FEATURE:
<221> NAME/KEY: MOD_RES
<222> LOCATION: (33)..(38)
<223> OTHER INFORMATION: Gly or Ala
<220> FEATURE:
<221> NAME/KEY: MISC_FEATURE
<222> LOCATION: (37)..(38)
<223> OTHER INFORMATION: May or may not be present
<220> FEATURE:
<221> NAME/KEY: MOD_RES
<222> LOCATION: (39)..(39)
<223> OTHER INFORMATION: Beta-Ala
<220> FEATURE:
<223> OTHER INFORMATION: See specification as filed for detailed
      description of substitutions and preferred embodiments

<400> SEQUENCE: 9

Arg Xaa Xaa Xaa Xaa Xaa Arg Arg Xaa Xaa Xaa Xaa Xaa Arg
1               5                   10                  15

Arg Xaa Xaa Xaa Xaa Xaa Xaa Arg Arg Xaa Xaa Xaa Xaa Xaa Arg
                20                  25                  30

Xaa Xaa Xaa Xaa Xaa Xaa Ala
                35

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccaccgcaaa tgcttctaga c                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11 ccccccccatt gagaagattc                                               20

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ctccacctcc agcacgcgac ttct                                           24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acgacgacga cgacgacgac gacga                                          25

<210> SEQ ID NO 14
<211> LENGTH: 750
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cugcugcugc ugcugcugcu gcugcugcug cugcugcugc ugcugcugcu gcugcugcug    60
cugcugcugc ugcugcugcu gcugcugcug cugcugcugc ugcugcugcu gcugcugcug   120
cugcugcugc ugcugcugcu gcugcugcug cugcugcugc ugcugcugcu gcugcugcug   180

```
cugcugcugc ugcugcugcu gcugcugcug cugcugcugc ugcugcugcu gcugcugcug      240
cugcugcugc ugcugcugcu gcugcugcug cugcugcugc ugcugcugcu gcugcugcug      300
cugcugcugc ugcugcugcu gcugcugcug cugcugcugc ugcugcugcu gcugcugcug      360
cugcugcugc ugcugcugcu gcugcugcug cugcugcugc ugcugcugcu gcugcugcug      420
cugcugcugc ugcugcugcu gcugcugcug cugcugcugc ugcugcugcu gcugcugcug      480
cugcugcugc ugcugcugcu gcugcugcug cugcugcugc ugcugcugcu gcugcugcug      540
cugcugcugc ugcugcugcu gcugcugcug cugcugcugc ugcugcugcu gcugcugcug      600
cugcugcugc ugcugcugcu gcugcugcug cugcugcugc ugcugcugcu gcugcugcug      660
cugcugcugc ugcugcugcu gcugcugcug cugcugcugc ugcugcugcu gcugcugcug      720
cugcugcugc ugcugcugcu gcugcugcug                                      750

<210> SEQ ID NO 15
<211> LENGTH: 270
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cugcugcugc ugcugcugcu gcugcugcug cugcugcugc ugcugcugcu gcugcugcug       60
cugcugcugc ugcugcugcu gcugcugcug cugcugcugc ugcugcugcu gcugcugcug      120
cugcugcugc ugcugcugcu gcugcugcug cugcugcugc ugcugcugcu gcugcugcug      180
cugcugcugc ugcugcugcu gcugcugcug cugcugcugc ugcugcugcu gcugcugcug      240
cugcugcugc ugcugcugcu gcugcugcug                                      270

<210> SEQ ID NO 16
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cugcugcugc ugcugcugcu gcugcugcug cug                                   33

<210> SEQ ID NO 17
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cugcugcugc ugcugcugcu gcug                                             24
```

PEPTIDE-LINKED MORPHOLINO ANTISENSE OLIGONUCLEOTIDES FOR TREATMENT OF MYOTONIC DYSTROPHY

CROSS REFERENCE TO RELATED APPLICATIONS

This application is a 371 National Phase Entry application of co-pending International Application No. PCT/US2013/061320, filed Sep. 24, 2013, which claims the benefit under 35 U.S.C. § 119 of United States Provisional Application 61/705,335, filed Sep. 25, 2012, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 18, 2016, is named US2012097USPCT_SL.txt and is 11,200 bytes in size.

FIELD OF THE INVENTION

This invention pertains to cationic peptide-linked morpholino (PPMO) antisense oligonucleotides that target the poly CUG repeat tract in the 3' untranslated region of the gene encoding dystrophia myotonica-protein kinase (DMPK) and systemic administration of the same for the treatment of mytonic dystrophy type I (DM1).

BACKGROUND

Myotonic dystrophy type 1 (DM1) is an autosomal dominant inherited disorder that manifests primarily as a neuromuscular disease but can also involve cardiac, endocrine, gastrointestinal, and central nervous system dysfunction. A hallmark symptom of DM1 is myotonia, a defect in muscle relaxation following contraction and detected by electromyography (EMG) as long runs of repetitive action potentials in muscle. The genetic lesion in DM1 consists of an unstable CUG trinucleotide repeat element in the 3' untranslated region of a gene encoding a protein kinase known as dystrophia myotonica-protein kinase (DMPK). A small number of copies of the CUG repeat are found in unaffected individuals, whereas large numbers of unstable CUG repeats, ranging from 50 copies to several thousand copies, are detected in DM1 patients. Genetic studies have established that the number of CUG repeats correlates directly with the age of onset and disease severity (Day & Ranum, 2005, *Neuromuscul Disord* 15:5-16).

RNA transcripts such as DMPK that contain a large number of CUG repeats acquire gain-of-function properties and promote RNA-mediated toxicity in cells and tissues expressing the mutant DMPK transcript (Wheeler & Thornton, 2007, *Curr Opin Neurol* 20:572-576). The pathogenic transcript is retained in the nucleus (Taneja et al., 1995, *J Cell Biol* 128:995-1002) where it entraps RNA binding proteins such as MBNL1 (Mankodi et al., 2001, *Hum Mol Genet* 10:2165-2170; Mankodi et al., 2003, *Ann Neurol* 54:760-768). Poly (CUG) RNA also increases steady-state levels of CUG-BP1 (Timchenko NA et al., 2001, *J Biol Chem*, 276:7820-7826; Kuyumcu-Martinez et al., 2007, *Mol Cell* 28:68-78). Both sequestration of MBNL1 and an increase in CUG-BP 1 activity is associated with abnormal splicing of a large number of RNA transcripts. Of note is the defective RNA splicing of chloride channel C1C-1 mRNA (Mankodi et al., 2002, *Mol Cell* 10:35-44), which has been shown to directly result in myotonia (Wheeler et al., 2007, *J Clin Invest* 117:3952-3957). In addition to abnormal RNA splicing, a consequence of mutant DMPK expression includes a remodeling of the skeletal muscle transcriptome (Osborne et al., 2009, *Hum Mol Genet* 18:1471-1481). Protein products with altered primary sequences resulting from abnormal RNA splicing and the dysregulated mRNA levels comprising the altered transcriptome would be expected to have associations and even causal relationships with specific aspects of DM1 disease.

There are currently no therapeutic agents in the clinic for DM1 that target toxic RNA, the primary pathogenic driver of the disease. Standard-of-care therapies for DM1 are mainly supportive and aimed at managing specific symptoms, e.g. myotonia (Logigian et al., 2010, *Neurology* 74:1441-1448). Pre-clinical evaluation of novel therapeutic approaches have been conducted in the HSA$^{LR}$ transgenic mouse model that contains a human skeletal actin transgene harboring a 250 CUG trinucleotide (SEQ ID NO: 14) insertion in the 3' untranslated region. The HSA$^{LR}$ model demonstrates several features of DM1 including MBNL1 sequestration by CUG RNA and the ensuing RNA splicing abnormalities, alterations in the muscle transcriptome, and physiological aberrations such as myotonia (Osborne et al., 2009, *Hum Mol Genet* 18:1471-1481; Mankodi et al., (2000), *Science* 289:1769-1773). Novel therapeutic modalities tested in the HSA$^{LR}$ mouse include small molecule ligands that are designed to interact with CUG repeat RNA and liberate foci-associated MBNL1 protein (Warf et al., 2009, *Proc Natl Acad Sci USA* 106:18551-18556; Parkesh et al., 2012, *J Am Chem Soc* 134:4731-4742; Ofori et al., 2012, *Nucl. Acid. Res. in press*, first published online: Apr. 6, 2012). In addition, three antisense oligonucleotide (ASO) chemistries that target the CUG repeat tract have been assessed in studies conducted in transgenic mouse models of DM1 (Wheeler et al., 2009, *Science* 325:336-339; Mulders et al., 2009, *Proc Natl Acad Sci U S A* 106:13915-13920; Lee et al., 2012, *Proc Natl Acad Sci USA* 109:4221-4226. Wheeler and colleagues (2009, *Science* 325:336-339) demonstrated local correction of DM1 pathology in tibilias anterior (TA) muscle of HSA$^{LR}$ mice subjected to intramuscular (IM) injection of a 25 mer morpholino oligonucleotide of CAG sequence (CAG25). The CAG25-treated TA muscles showed a decrease in the presence of ribonuclear foci, re-distribution of MBNL1 protein, correction of abnormal RNA splicing, restoration of chloride channel (CIC-1) protein expression and function, and reduction of myotonia (Wheeler et al., 2009, *Science* 325:336-339). Although this therapeutic approach showed corrections in the DM1-like phenotype of HSA$^{LR}$ mice, thereremains a need for a systemic delivery strategy that would allow multiple tissues, including multiple tissue types, to gain exposure to active morpholino oligonucleotide targeted at the toxic DMPK RNA transcripts responsible for DM1.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions and methods for the fabrication and use of cationic peptide-linked morpholino (PPMO) antisense oligonucleotides which can be systemically delivered to multiple tissues and tissue types and use of the same for treatment of DM1.

Accordingly, in one aspect, provided herein is a method for treating or preventing myotonic dystrophy type1 (DM1) in an individual in need thereof comprising: systemically administering to the individual a therapeutically effective amount of a cationic peptide-linked morpholino antisense oligonucleotide comprising a sequence complementary to at least 3polyCUG repeat sequences in a 3' untranslated region (UTR) of a dystrophia myotonica protein kinase (DMPK) RNA transcript target, wherein administration of the cationic peptide-linked morpholino antisense oligonucleotide relieves at least one symptom of DM1 in at least two muscles. The method of claim 1, wherein the cationic peptide is 8-30 amino acid residues in length and comprises one or more subsequences selected from the group consisting of RXR, RX, RB, and RBR, wherein R is arginine, B is β-alanine, and each X is independently —NH—(CHR$^1$)$_n$—C(O)—, wherein n is 4-6 and each R$^1$ is independently H or methyl such that at most two R$^1$s are methyl. In some embodiments, the cationic peptide comprises the amino acid sequence Ac(RXRRBR)$_2$XB- (SEQ ID NO: 1). In other embodiments, the cationic peptide comprises the amino acid sequence Ac(RXR)$_4$XB- (SEQ ID NO: 2). In some embodiments of any of the methods described above, the cationic peptide-linked morpholino antisense oligonucleotide comprises the sequence 5' -(AGC)$_n$ -3' (SEQ ID NO: 3), 5' -(GCA)$_n$ -3' (SEQ ID NO: 4), or 5' -(CAG)$_n$ -3' (SEQ ID NO: 5), wherein n is any of about 5-25. In another embodiment, the cationic peptide-linked morpholino antisense oligonucleotide further comprises 1 to 2 additional morpholino nucleotides on the 5' and/or the 3' end of the oligonucleotide. In some embodiments, the cationic peptide-linked morpholino antisense oligonucleotide comprises the sequence: 5'-AGCAGCAGCAGCAGCAGCAGCA-3' (SEQ ID NO: 6). In another embodiment, the cationic peptide-linked morpholino antisense oligonucleotide further comprises a 5' amine modification. In some embodiments of any of the methods described above, the cationic peptide-linked morpholino antisense oligonucleotide is a phosphorodiamidate cationic peptide-linked morpholino antisense oligonucleotide. In other embodiments of any of the methods described above, the cationic peptide is separated from the morpholino antisense oligonucleotide by a spacer moiety linked at the 5' end of the morpholino antisense oligonucleotide. In one embodiment, the spacer moiety comprises

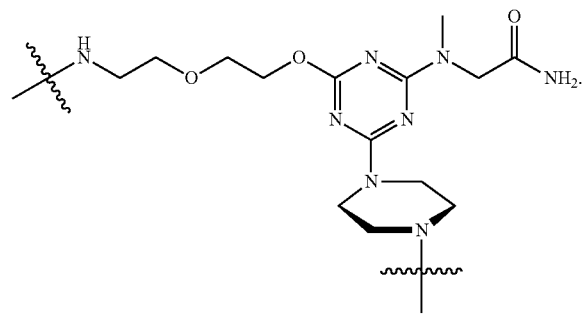

In some embodiments of any of the methods described above, the muscles are skeletal muscles, smooth muscles, and/or cardiac muscle. In other embodiments of any of the methods described above, the cationic peptide-linked morpholino antisense oligonucleotide penetrates into cells of the tibialis anterior muscle, the quadriceps muscle, and/or the gastrocnemius muscle. In yet other embodiments of any of the methods described above, said at least one symptom of DM1 is myotonia. In some embodiments of any of the methods described above, said at least one symptom of DM1 is aggregation of musclebind-like-1 (MBNL-1) protein in ribonuclear foci within myonuclei. In other embodiments of any of the methods described above, said at least one symptom of DM1 is abnormal splicing of at least one RNA transcript in muscle cells. In another embodiment, said at least one RNA transcript (such as RNA transcript of human genes) is selected from the group consisting of: Serca-1, m-Titin, Zasp, and ClC. In some embodiments of any of the methods described above, systemic administration of the cationic peptide-linked morpholino antisense oligonucleotide is performed intravenously, intraperitoneally, or subcutaneously. In other embodiments of any of the methods described above, the cationic peptide-linked morpholino antisense oligonucleotide is administered to the individual weekly. In still other embodiments of any of the methods described above, the cationic peptide-linked morpholino antisense oligonucleotide is administered to the individual for one to six weeks. In some embodiments of any of the methods described above, the cationic peptide-linked morpholino antisense oligonucleotide is administered with a pharmaceutically acceptable excipient. In other embodiments of any of the methods described above, the individual is a human.

DETAILED DESCRIPTION OF THE INVENTION

Figure 1:
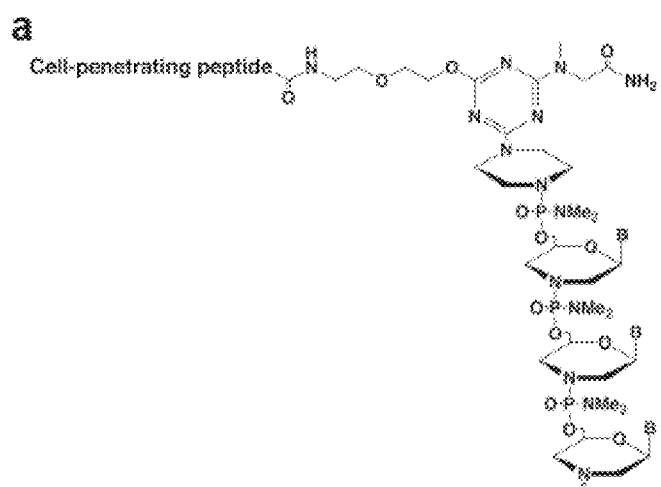
FIG. 1 depicts the chemical structure of PPMO and evaluation of the bio-activity of PPMO-B and PPMO-K in HSA$^{LR}$ mice. (a) Structure of a PPMO containing a cell-penetrating peptide (peptide B or peptide K) covalently appended to a linker located at the 5' end of a morpholino oligomer. Sequences of peptide B and peptide K are described in the Material and Methods. (b) IM injection of test and control ASOs in TA muscle was performed as described in the Materials and Methods. Direct injection into TA with subsequent analysis of Serca-1 splicing served to determine the impact of covalent attachment of peptide B or peptide K upon the bioactivity of CAG25. Three weeks following IM injection, TA muscles were harvested, total RNA was purified, and Serca-1 was amplified to detect splice isoforms with or without exon 22 (ex22). Each bracket represents one HSA$^{LR}$ mouse injected with the indicated ASO (GAC25, CAG25, PPMO-B, and PPMO-K) injected into one TA and the contralateral TA (con) injected with saline vehicle. RNA from the TA of a FVB/n wild-type mouse was also analyzed as a control and demonstrates splicing of Serca-1 that occurs in non-disease mice.
Figure 1:
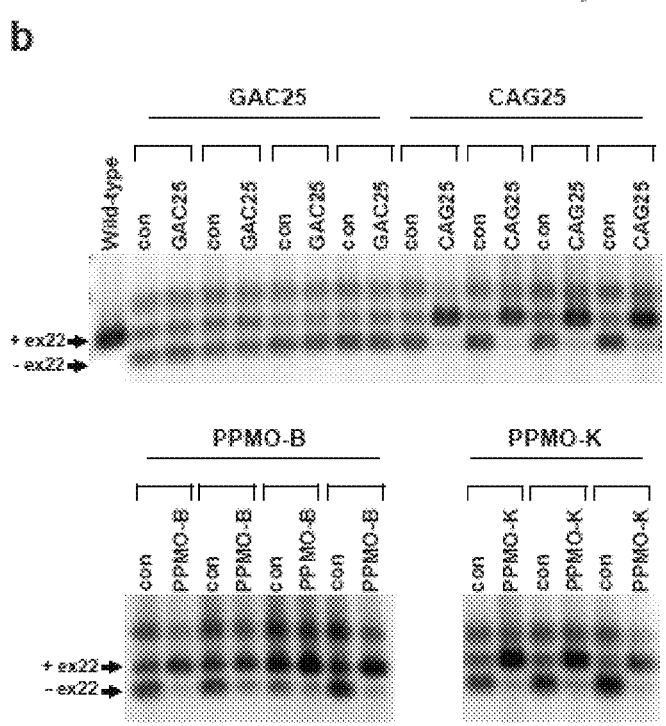

This invention provides, inter alia, cationic peptide-linked morpholino (PPMO) antisense oligonucleotides which can be systemically delivered to multiple tissues and/or tissue types in individuals with myotonic dystrophy type 1 (DM1). The inventors have discovered that the addition of a cell penetrating peptide to a CAG sequence morpholino permits sufficient uptake of PPMO into muscle tissue to neutralize the toxic effects of an elongated CUG repeat when administered systemically in animal models of DM1. Delivery of these morpholinos and penetration of them into muscle cells of individuals possessing high numbers of poly CUG mRNA was associated with near complete resolution of splicing defects in a number of proteins, release of MBNL1 from RNA foci, and elimination of myotonia.

I. General Techniques

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994). Nucleic acids can be synthesized in vitro by well-known chemical synthesis techniques, as described in, e.g., Carruthers (1982) Cold Spring Harbor *Symp. Quant. Biol.* 47:411-418; Adams (1983) *J. Am. Chem. Soc.* 105:661; Belousov (1997) *Nucleic Acids Res.* 5 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; U.S. Pat. No. 4,458,066.

II. Definitions

The term "RNA target" refers to an RNA transcript to which a morpholino binds in a sequence specific manner. In some embodiments the RNA target is one or more DMPK mRNA molecules having a variable number of CUG trinucleotide repeat elements in the 3' untranslated region.

"Morpholino" or "morpholino antisense oligonucleotide" refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide. In some embodiments, the morpholino binds to an RNA target which blocks translation of the RNA target into a protein. In other embodiments, the morpholino prevents aggregation of the RNA target with itself or with other cellular RNAs, proteins, or riboproteins, such as, but not limited to, RNAs, proteins, and riboproteins associated with the cellular mRNA splicing apparatus.

An "individual" can be a mammal, such as any common laboratory model organism, or a mammal Mammals include, but are not limited to, humans and non-human primates, farm animals, sport animals, pets, mice, rats, and other rodents.

As used herein, "treatment" (and grammatical variations thereof such as "treat" or "treating") refers to clinical intervention designed to alter the natural course of the individual or cell being treated during the course of clinical pathology. Desirable effects of treatment include, but are not limited to, decreasing the rate of disease progression, amelioration or palliation of the disease state, and remission or improved prognosis.

As used herein, "prevention" includes providing prophylaxis with respect to occurrence or recurrence of a disease or the symptoms associated with a disease in an individual. An individual may be predisposed to, susceptible to, or at risk of developing a disease, but has not yet been diagnosed with the disease.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect. For an antisense oligomer, this effect is typically brought about by inhibiting translation or natural splice-processing of a selected target sequence.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Compositions

A. Morpholinos

Morpholinos are synthetic molecules having a structure that closely resembles a naturally occurring nucleic acid. These nucleic acids bind to complementary RNA sequences by standard nucleic acid basepairing. Structurally, morpholinos differ from DNA or RNA in that these molecules have nucleic acid bases bound to morpholine rings instead of deoxyribose or ribose rings. Additionally, the backbone structure of morpholinos consists of non-ionic or cationic linkage groups instead of phosphates. For example, replacement of anionic phosphates with the uncharged phosphorodiamidate groups eliminates ionization in the usual physiological pH range, making morpholinos in organisms or cells uncharged molecules. Morpholinos are most commonly used as single-stranded oligos, though heteroduplexes of a morpholino strand and a complementary DNA strand may be used in combination with cationic cytosolic delivery reagents.

Unlike many antisense structural types (e.g., phosphorothioates), morpholinos do not degrade their target RNA molecules. Instead, morpholinos act by "steric blocking," i.e., binding to a target sequence within an RNA and sterically hindering molecules which might otherwise interact with the RNA. Bound to the 5'-untranslated region of messenger RNA (mRNA), morpholinos can interfere with progression of the ribosomal initiation complex from the 5' cap to the start codon. This prevents translation of the coding region of the targeted transcript (called "knocking down" gene expression). Some morpholinos knock down expression so effectively that after degradation of preexisting proteins the targeted proteins become undetectable by Western blot.

Morpholinos can also interfere with pre-mRNA processing steps, usually by preventing splice-directing snRNP complexes from binding to their targets at the borders of introns on a strand of pre-RNA. Preventing U1 (at the donor site) or U2/U5 (at the polypyrimidine moiety and acceptor site) from binding can result in modified splicing, commonly leading to the exclusion of exons from a mature mRNA transcript. Splice modification can be conveniently assayed by reverse-transcriptase polymerase chain reaction (RT-PCR) and is seen as a band shift after gel electrophoresis of RT-PCR products.

Morpholinos have also been used to block intronic splice silencers and splice enhancers. U2 and U12 snRNP functions have been inhibited by morpholinos. Morpholinos targeted to "slippery" mRNA sequences within protein coding regions can induce translational frameshifts. Activities of morpholinos against this variety of targets suggest that morpholinos can be used as a general-purpose tool for blocking interactions of proteins or nucleic acids with mRNA.

The compositions of the present invention are composed of morpholino subunits linked together by uncharged phosphorus-containing linkages, one to three atoms long, joining the morpholino nitrogen of one subunit to the 5' exocyclic carbon of an adjacent subunit, wherein the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine Preparation of such oligomers is described in detail in U.S. Pat. No. 5,185,444, which is hereby incorporated by reference in its entirety. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino The pendant nitrogen attached to phosphorus may be unsubstituted, monosubstituted, or disubstituted with (optionally substituted) lower alkyl. The purine or pyrimidine base pairing moiety is typically adenine, cytosine, guanine, uracil, thymine or inosine. The synthesis, structures, and binding characteristics of morpholinos are detailed in U.S. Pat. Nos. 5,698,685, 5,217,866, 5,142,047, 5,034,506, 5,166, 315, 5,521,063, 5,506,337, and International Patent Application Publication No. WO 2008/036127 all of which are incorporated herein by reference.

In some aspects, the morpholino antisense oligonucleotides of the present invention can be complementary to polyCUG repeat sequences in a 3' untranslated region (UTR) of a dystrophia myotonica protein kinase (DMPK) RNA target. In some embodiments, the morpholino antisense oligonucleotide is at least any of about 90%, 95%, or 100%, inclusive, including any percentages in between these values, identical to a 3' untranslated region of dystrophia myotonica protein kinase (DMPK) RNA target. In some embodiments, the morpholino antisense oligonucleotides are complementary to at least any of 3, 4, 5, 6, 7, 8, 9, 10, 11, 12, 13, 14, 15, 16, 17, 18, 19, 20, 21, 22, 23, 24, or 25 or more polyCUG repeat sequences in the 3' untranslated region (UTR) of a DMPK RNA target. In some embodiments, the cationic peptide-linked morpholino antisense oligonucleotide comprises the sequence 5'-(AGC)$_n$-3' (SEQ ID NO: 3), 5'-(GCA)$_n$-3' (SEQ ID NO: 4), or 5-(CAG)$_n$-3' (SEQ ID NO: 5), wherein n is any of about 5-25. In another embodiment, the cationic peptide-linked morpholino antisense oligonucleotides can further comprise 1 to 2 additional morpholino nucleotides on the 5' and/or 3' end of the oligonucleotides. In some embodiments, the morpholino antisense oligonucleotide comprises the sequence 5'-AGCAGCAGCAGCAGCAGCAGCAGCA-3' (SEQ ID NO: 6). In another embodiment, the morpholino antisense oligonucleotide binds to the DMPK RNA transcript in a sequence-specific manner. In some embodiments, the morpholino antisense oligonucleotide comprises a 5' amine modification. In another embodiment, the morpholino antisense oligonucleotide can be a phosphorodiamidate cationic peptide-linked morpholino antisense oligonucleotide.

B. Cationic cell-penetrating peptides and cationic peptide-linked morpholinos

The morpholino antisense oligonucleotides described herein are linked to a cationic peptide which facilitates systemic delivery of the morpholino antisense oligonucleotides into muscle cells. In general, a cationic peptide as described herein can be 8 to 30 amino acid residues in length and consist of subsequences selected from the group consisting of RXR, RX, RB, and RBR; where R is arginine (which may include D-arginine), B is β-alanine, and each X is independently —NH—$(CHR^1)_n$—C(O)—, where n is 4-6 and each $R^1$ is independently H or methyl, such that at most two $R^1$'s are methyl. In some embodiments, each $R^1$ is hydrogen. In other embodiments, the cationic peptide can be any of 8, 9, 10, 11, 12, 13, 14, 15, 16, 17, 18, 19, 20, 21, 22, 23, 24, 25, 26, 27, 28, 29, or 30 amino acid residues in length. In another embodiment, the variable n is 5, e.g. as in 6-aminohexanoic acid. In one embodiment, the cationic peptide comprises the amino acid sequence Ac(RXRRBR)$_2$XB- (SEQ ID NO: 8), where Ac is an acetyl group. In another embodiment, the cationic peptide comprises the amino acid sequence Ac(RXR)$_4$XB- (SEQ ID NO: 9), where Ac is an acetyl group. Further information regarding synthesis and structure of cationic cell-penetrating peptides can be found in U.S. Patent Application Publication No. 2009/0099066, the disclosure of which is incorporated by reference herein in its entirety.

In one aspect, the cationic peptide is linked directly to the morpholino antisense oligonucleotide. In other embodiments, the cationic peptide is linked to the morpholino antisense oligonucleotide via a spacer moiety linked to the 5' end of the morpholino antisense oligonucleotide. The spacer moiety may be incorporated into the peptide during cationic peptide synthesis. For example, where a spacer contains a free amino group and a second functional group (e.g., a carboxyl group or an amino group) that enables binding to another molecular moiety, the spacer may be conjugated to a solid support used for peptide synthesis. Thereafter, the cationic peptide may be synthesized directly onto the spacer's free amino group by standard solid phase techniques. In another embodiment, the spacer moiety may be conjugated to the cationic peptide after peptide synthesis. Such conjugation may be achieved by methods well established in the art. In one embodiment, the linker contains at least one functional group suitable for attachment to the target functional group of the synthesized cationic peptide. For example, a spacer with a free amine group may be reacted with the cationic peptide's C-terminal carboxyl group. In some embodiments, the spacer m ty comprises:

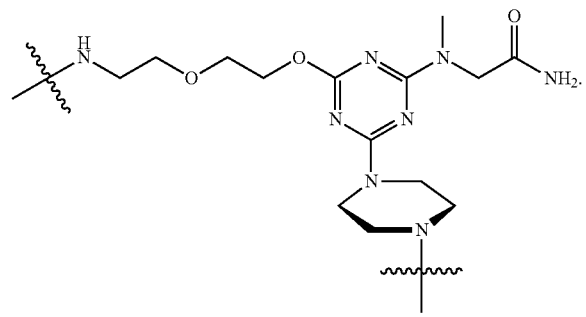

In one embodiment, the cationic peptide-linked morpholino antisense oligonucleotides have the following structure:

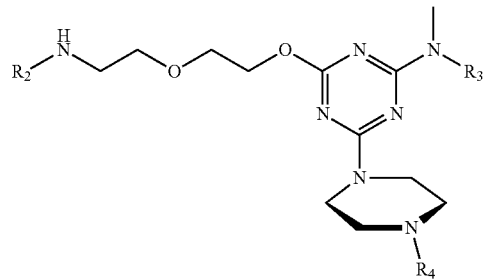

wherein $R^2$ is a cationic peptide (such as any of the cationic peptides disclosed herein), $R^3$ is H, $CH_3$ or $CH_2CONH_2$, and $R^4$ is a morpholino antisense oligonucleotide comprising the sequence 5'-(AGC)$_n$-3' (SEQ ID NO: 3), 5'-(GCA)$_n$-3' (SEQ ID NO: 4), or 5'-(CAG)$_n$-3' (SEQ ID NO: 5), wherein n is any of about 5-25. In another embodiment, the cationic peptide-linked morpholino antisense oligonucleotides can further comprise 1 to 2 additional morpholino nucleotides on the 5' and/or 3' end of the oligonucleotides.

In another aspect, the cationic peptide linked morpholino antisense oligonucleotide comprises

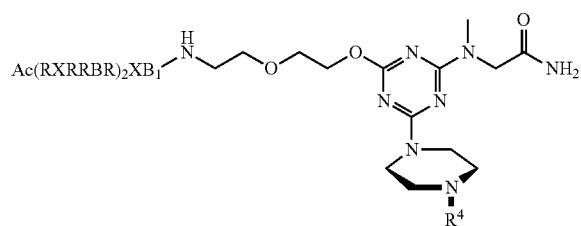

wherein Ac is acetyl, R is arginine (which may include D-arginine), B is β-alanine, each X is independently —NH—$(CHR^1)_n$—C(O)—, where n is 4-6 and each $R^1$ is H, and $R^4$ is a morpholino antisense oligonucleotide comprising the sequence 5'-AG(CAG)$_7$CA -3' (SEQ ID NO: 6). The structure above discloses the peptide "Ac(RXRRBR)$_2$XB" as SEQ ID NO: 8.

In another aspect, the cationic peptide linked morpholino antisense oligonucleotide comprises

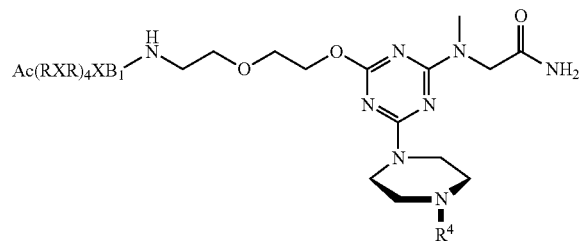

wherein Ac is acetyl, R is arginine (which may include D-arginine), B is β-alanine, each X is independently —NH—$(CHR^1)_n$—C(O)—, where n is 4-6 and each $R^1$ is H, and $R^4$ is a morpholino antisense oligonucleotide comprising the sequence 5'-AG(CAG)$_7$CA -3' (SEQ ID NO: 6). The structure above discloses the peptide "Ac(RXR)$_4$XB" as SEQ ID NO: 9.

C. Pharmaceutical Formulations

When employed as pharmaceuticals, the cationic peptide-linked morpholino antisense oligonucleotides disclosed herein can be formulated with a pharmaceutically acceptable excipient or carriers to be formulated into a pharmaceutical composition.

When employed as pharmaceuticals, the cationic peptide-linked morpholino antisense oligonucleotides can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the cationic peptide-linked morpholino antisense oligonucleotides associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 mg to about 100 mg or more, such as any of about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, or about 5 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The cationic peptide-linked morpholino antisense oligonucleotides are effective over a wide dosage range and are generally administered in a therapeutically effective amount. It will be understood, however, that the amount of the cationic peptide-linked morpholino antisense oligonucleotides actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient/cationic peptide-linked morpholino antisense oligonucleotide is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may also be administered, orally or nasally, from devices which deliver the formulation in an appropriate manner.

IV. Methods of the Invention

The cationic peptide-linked morpholino (PPMO) antisense oligonucleotides (such as in compositions) disclosed herein can be used for the treatment and/or prevention of symptoms of myotonic dystrophy type I (DM1) in an individual. In some aspects, the individual is at risk of developing DM1. In some aspects, the method can comprise treating and/or preventing symptoms associated with DM1 (such as any of the symptoms described herein) in an individual by systemically administering to the individual an effective amount of the cationic peptide-linked morpholino (PPMO) antisense oligonucleotides or compositions comprising the same disclosed herein. In some embodiments, the individual is diagnosed with or is suspected of having DM1.

The present invention is directed to methods for inhibiting the symptoms or conditions (disabilities, impairments) associated with DM1 as described in detail below. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition resulting from DM1, but rather, can encompass a result which includes reducing or preventing the symptoms that result from DM1, reducing or preventing the occurrence of such symptoms (either quantitatively or qualitatively), reducing the severity of such symptoms or physiological effects thereof, and/or enhancing the recovery of the individual after experiencing DM1 symptoms.

Provided in another aspect are methods for reducing the aggregation of one or more DMPK mRNA transcripts within a cell. In some embodiments, the method prevents aggregation of one or more DMPK mRNA transcripts in the nucleus of the cell.

In another aspect, provided herein are methods for reducing the aggregation of one or more DMPK mRNA tranpscripts and one or more nuclear proteins or RNAs within a cell. In some embodiments, the one or more nuclear proteins are proteins involved in splicing pre-mRNAs (a.k.a. heteronuclear RNAs (hnRNAs)) into mature spliced mRNAs. In one embodiment, the nuclear proteins are small core proteins (a.k.a. Sm proteins) and can be one or more of SmB, SmB', SmD1, SmD2, SmD3, SmE, SmF, SmG, or SmN. In some embodiments, the one or more nuclear RNAs are RNAs involved in splicing hnRNAs into mature spliced mRNAs. In another embodiment, the nuclear RNAs are small nuclear RNAs (snRNAs) and can be one or more of U1, U2, U3, U4, U5, U6, U11, U12, U4atac, or U6atac. In some embodiments, the one or more nuclear proteins or RNAs comprise a nuclear riboprotein complex. In another embodiment, the RNAs can be an RNA that is not part of the cellular splicing apparatus, such as Serca-1, m-Titin, Zasp, and ClC-1. In one embodiment the cell is a muscle cell, such as a skeletal muscle cell, a smooth muscle cell, or a cardiac muscle cell.

Specifically, a composition of the present invention, when administered to an individual, may treat or prevent one or more of the symptoms or conditions associated with DM1 and/or reduce or alleviate symptoms of or conditions associated with this disorder. As such, protecting an individual from the effects or symptoms resulting from an DM1 includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not.

A. Myotonic Dystrophy

Myotonic dystrophy (a.k.a, dystrophia myotonica or myotonia atrophica) is a chronic, slowly progressing, highly variable, inherited multisystemic disease with predominant symptoms that include muscle wasting (muscular dystrophy), cataracts, heart conduction defects, endocrine changes, and myotonia. Myotonic dystrophy type 1 (DM1), otherwise known as "Steinert disease," has both a severe congenital form and a milder childhood-onset form and results from mutation of a gene called dystrophia myotonica protein kinase (DMPK), a protein expressed predominantly in skeletal muscle located on the long arm of chromosome 19. Myotonic dystrophy type 2 (DM2), also called proximal myotonic myopathy (PROMM), is rarer than DM1 and generally manifests with milder signs and symptoms. DM2 is proximally caused by a defect of the ZNF9 gene on chromosome 3. Myotonic dystrophy can occur in patients of any age and forms of the disease display an autosomal dominant pattern of inheritance. DM1 is the most common form of muscular dystrophy diagnosed in adults, with a prevalence ranging from 1 per 100,000 in Japan to 3-15 per 100,000 in Europe (Turner & Hilton-Jones, 2010, *J Neurol Neurosurg Psychiatry* 81:358-367).

The age of onset as well as the severity of symptoms in individuals afflicted with DM1 can vary significantly, even between genetically related individuals. In some individuals, symptoms can manifest at birth or not become apparent until well into old age. DM1 is a progressive disorder, with symptoms generally becoming worse slowly over time. Consequently, individuals whose symptoms manifest early in life typically experience both a greater number of complications and more severe symptoms in comparison to those individuals who do not present with symptoms typical of the disorder until later in life. Nevertheless, individual prognosis varies and cannot be accurately predicted with respect to how the disease will affect any one individual.

1. Cardiovascular Symptoms

Some individuals with DM1 can experience moderate to severe cardiopulmonary defects. For example, sudden death due to complete cardiac conduction block and ventricular fibrillation/tachycardia caused by cardiomyopathy has been attributed to DM1 in some cases. Other cardiovascular symptoms that have been associated with DM1 include, but are not limited to, cardiogenic syncope and presyncope, cardiac conduction defects, cardiac arrhythmias, hypotension, and congestive heart failure. Often, individuals diagnosed with DM1 develop cardiovascular symptoms subsequent to the onset of other neuromuscular symptoms. However, some data indicates that asymptomatic children have an observable risk for sudden cardiac death.

2. Central Nervous System Symptoms

Excessive daytime sleepiness (hypersomnia) is often observed in individuals with DM1 irrespective of the age of onset. While generalized fatigue is also commonly observed in DM1, hypersomnia is characterized by a need to sleep frequently, and often unpredictably, during the day despite normal or greater than normal duration of sleep at night.

While significant peripheral nerve abnormalities have not been confirmed in individuals diagnosed with DM1, some minor abnormalities in peripheral nerve function have been confirmed by nerve conduction studies. The proximate cause of DM1-indiced peripheral nerve dysfunction is not currently known.

3. Gastrointestinal Tract Symptoms

Gastrointestinal symptoms are commonly observed in DM1 and result from dysfunction of digestive tract skeletal and/or smooth muscles. Included in these symptoms are difficulty swallowing due to mouth, tongue or throat weakness/myotonia, gastroesophageal reflux due to esophageal sphincter laxity, abdominal pain, nausea, vomiting, bloating or bowel pseudo-obstruction due to ineffective peristaltic smooth muscle contraction in the gut and stomach, gall stones resulting from weak/myotonic bile duct/gall bladder musculature, constipation, diarrhea or malabsorption caused by bowel dysmotility, and fecal incontinence due to anal sphincter and pelvic floor muscle weakness.

4. Reproductive and Endocrine System Symptoms

DM1 is associated with significant reproductive and endocrine system abnormalities. In men, these symptoms may not be recognized until adulthood when the hormonal and endocrine changes associated with puberty fail to occur or are delayed. In males, DM1 is associated with testicular atrophy which can result in decreased or absent sperm production and male infertility, poor development of secondary sex characteristics, including decreased energy, libido, sexual hair, muscle mass, and bone mineral density. Furthermore, males with DM1 frequently experience low serum testosterone levels accompanied by elevated serum luteinizing hormone and follicle stimulating hormone levels. Elevated FSH levels are associated with abnormally high estradiol:testosterone ratios, which can lead to breast enlargement in males. Finally, males with DM1 often experience high rates of frontal male pattern baldness and hair loss.

5. Respiratory Symptoms

Due to muscle weakness in the diaphragm, abdominal, and intercostals muscles as well as myotonia of respiratory muscles, DM1 can be associated with respiratory failure and, in the most severe cases, may require mechanical ventilation to assist the individual to breath. Additionally, due to weakness in these muscles, an individual with DM1 often lacks the strength to cough following unintended aspiration of food and drink, saliva, nasal secretions, and stomach fluids, into the lungs that often accompany the difficulty with swallowing characteristic of the disease. This can lead to injury and inflammation of the lungs and bronchial tubes resulting in infection.

Another respiratory symptom affecting individuals with DM1 is sleep apnea, which is a sleep disorder characterized by abnormal pauses in breathing or instances of abnormally low breathing, during sleep brought about in DM1 by respiratory muscle weakness. Each pause in breathing, called an apnea, can last from a few seconds to minutes, and may occur 5 to 30 times or more an hour. Insufficient airflow due to sleep apnea (periods of absent airflow due to narrow airways and interrupted breathing) can result in dangerously low levels of oxygen and high levels of carbon dioxide in the blood. In mild cases, apnea can cause disrupted sleep, excessive fatigue, and morning headaches. In severe cases, apnea can cause high blood pressure, cardiac arrhythmias, and heart attack.

6. Skeletal Muscle Symptoms

Individuals with DM1 commonly experience myotonia, which is characterized by the slow relaxation of the muscles after voluntary contraction or electrical stimulation. Generally, repeated effort is needed to relax the muscles, and the condition improves after the muscles have warmed up. However, prolonged, rigorous exercise may also trigger the condition. Individuals with the disorder may have trouble releasing their grip on objects or may have difficulty rising from a sitting position and a stiff, awkward gait. While any skeletal muscle may experience myotonia, DM1 has a tendency to afflict certain muscles of the body more frequently than others. These include the forearm and finger muscles and the muscles of the tongue and jaw, which can lead to trouble with speech or chewing food. Additionally, quick movements may sometimes trigger the muscle stiffness characteristic of myotonia in DM1.

Muscle weakness and atrophy are also observed in many individuals suffering from DM1. Muscular weakness in DM1 characteristically affects some muscles while other muscles may experience little to no weakness or may maintain normal strength. Muscle weakness is the primary cause of disability in individuals with DM1 and typically affects mobility, hand dexterity, and the ability to lift moderately heavy to heavy objects. In more severe cases, individuals experience trouble with breathing or swallowing, caused by weakness of the muscles in the throat and chest (e.g. the diaphragm muscle).

Furthermore, DM1 is often accompanied by muscle pain. The pain can affect the muscle itself or can have its source in joints, ligaments, or the spine. Additionally, muscle weakness may predispose individuals with DM1 to arthritic strain in these areas.

In females, DM1 is associated with moderate to severe complications associated with pregnancy and childbirth as well as reduced fertility. These can include early onset menopause, higher rates of spontaneous abortions and miscarriage, prolonged labor and delivery related to uterine dysfunction caused by muscle weakness or myotonia, uterine overdistention, related to polyhydramnios, which can cause preterm labour, inadequate uterine contractions (atonic uterus), or premature spontaneous rupture of membranes, as well as post-partum haemmorrhage due to inadequate uterine contractions (atonic uterus) or retained placenta.

In neonates, DM1 symptoms can include symptoms such as polyhydramnios (excessive accumulation of amniotic fluid due to decreased fetal swallowing) which is associated with increased risks of adverse pregnancy outcome, umbilical cord prolapse or placental abruption, fetal malposition due to greater fetal mobility, pre-term labor, fetal edema, and reduced fetal movement.

7. Vision Symptoms

Visual impairments in patients with DM1 are often associated with the development of cataracts. Posterior subcapsular iridescent lens opacities represent an initial phase of cataract formation in myotonic dystrophy and are detectable only with slit lamp biomicroscopy. These opacities are usually found in patients who have not developed any visual symptoms. The presence of this type of lens opacities and more mature cataracts may be the only sign of the disease. Glare and blurriness of the vision develop as the progression of the lens opacities into stellate cataracts and eventually mature cataracts, which are indistinguishable from usual cataracts. Cataracts in DM1 may progress faster than usual cataracts, and thus patients with DM1 may be presented with early-onset cataracts.

Additional visual symptoms associated with DM1 can include retinopathy, bilateral blepharoptosis (drooping or falling of the upper or lower eyelid), ocular hypotension, and ocular myotonia.

8. Cellular and Molecular Symptoms

The genetic lesion of DM1 results in a DMPK RNA transcript containing a large number of 3'-untranslated region CUG repeats which acquires gain-of-function properties and promotes RNA-mediated toxicity in cells and tissues expressing the mutant DMPK transcript. The current model of the disease process in DM1 relates to the interaction of $CUG^{exp}$ RNA with nuclear binding proteins ultimately leading to abnormal regulation of alternative splicing for a selected group of pre-mRNAs. The most prominent molecular defect identified in DM1 is misregulation of alternative splicing. While several human genetic disorders can be attributed to the effects of mutations on RNA splicing, almost all of these are cis-acting effects that affect splicing of a single pre-mRNA leading to aberrantly spliced transcripts encoding a non-functional, mutant protein (Osborne & Thornton, 2006, *Hum Mol Genet.*, 15;15 Spec No 2:R162-9; Faustino & Cooper, 2003, *Genes Dev.*, 17:419-437). DM1 is the first example of a human genetic disease resulting from spliceopathy, i.e. a trans-effect on the alternative splicing of many RNAs, which does not result in production of mutant protein but leads to expression of splice products that are developmentally inappropriate for a particular tissue (Osborne & Thornton, 2006, *Hum Mol Genet.*,15;15 Spec No 2:R162-9).

Muscleblind (MBNL) proteins were initially identified for binding $(CUG)_{90}$ (SEQ ID NO: 15) in preference to $(CUG)_{11}$ (SEQ ID NO: 16) in vitro (Miller et al., 2000, *EMBO J.*,19:4439-4448). These proteins are heavily recruited into nuclear foci in DM1 (Mankodi et al., 2003, *Ann. Neurol.*, 54:760-768). Of the three mammalian MBNL genes, MBNL1 and MBNL2 are expressed in skeletal muscle, heart and brain, and MBNL3 is expressed mainly in placenta (Osborne & Thornton, 2006, *Hum Mol Genet.*, 15;15 Spec No 2:R162-9). The level of $CUG^{exp}$ expressed in DM1 is sufficient to markedly alter the cellular distribution of MBNL1. In brain, skeletal muscle and heart, MBNL1 is recruited into ribonuclear foci to such an extent that it is markedly depleted elsewhere in the nucleoplasm (Jiang et al., 2004, *Hum. Mol. Genet.* 13:3079 -3088; Osborne & Thornton, 2006, *Hum Mol Genet.*, 15;15 Spec No 2:R162 -9). Disruption of the MBNL1gene in mice reproduces not only a myotonic myopathy similar to DM1, but also DM1-like cataracts and cardiac disease (Osborne & Thornton, 2006, *Hum Mol Genet.*, 15;15 Spec No 2:R162-9). Without being bound to theory, these findings suggest that sequestration of MBNL1protein on repeat expansion RNA plays an important role in the phenotype and symptoms associated with DM1.

Another protein thought to play a role in DM1 is CUG-BP1, which is also capable of inducing DM1-like effects on alternative splicing in muscle (Philips et al., 1998, *Science*, 280:737-741) and was first identified for binding to $(CUG)_8$ (SEQ ID NO: 17) oligonucleotides in vitro (Timchenko et al., 1996, *Nucleic Acids Res.*, 24:4407-4414). Also of note is the aberrant splicing of the chloride channel ClC-1 mRNA, which has been shown to directly result in myotonia (Mankodi et al., 2002, *Mol. Cell*, 10:35-44). Other proteins shown to have misregulated alternative splicing in skeletal muscles of individuals with DM1 include, but are not limited to, proteins encoded by the ALP, CAPN3, CLCN1, FHOS, GFAT1, IR, MTMR1, NRAP, RYR1, SERCA1, z-Titin, m-Titin, TNNT3, or ZASP genes. Proteins shown to have misregulated alternative splicing in cardiac muscle of individuals with DM1include, but are not limited to, proteins encoded by the TNNT2, ZASP, m-Titin, KCNAB1, or ALP genes. Proteins shown to have misregulated alternative splicing in neurological tissue of individuals with DM1 include, but are not limited to, proteins encoded by the TAU, APP, or NMDAR1 genes (Osborne & Thornton, 2006, *Hum Mol Genet.*, 15;15 Spec No 2:R162-9)

B. Methods of Treating Myotonic Dystrophy Type-I

Provided herein are methods for treating myotonic dystrophy type 1 (DM1) in an individual in need thereof comprising: systemically administering to the individual a therapeutically effective amount of a cationic peptide-linked morpholino antisense oligonucleotide (such as any of the cationic peptide-linked morpholino antisense oligonucleotides disclosed herein) comprising a sequence complementary to at least 3 polyCUG repeat sequences in a 3' untranslated region (UTR) of a dystrophia myotonica protein kinase (DMPK) RNA transcript, wherein administration of the cationic peptide-linked morpholino antisense oligonucleotide relieves at least one symptom of DM1 in at least two muscles. In one embodiment, the muscles can be skeletal muscles, smooth muscles, and/or cardiac muscle. In another embodiment, the muscles are skeletal muscles and can include, without limitation, the tibialis anterior muscle, the quadriceps muscle, and/or the gastrocnemius muscle. In some embodiments, administration of the cationic peptide-linked morpholino antisense oligonucleotide can be performed intravenously, intraperitoneally, or subcutaneously. In other embodiments, the cationic peptide-linked morpholino antisense oligonucleotide can be administered to the individual any of daily, every two days, every three days, every four days, every 5 days, every 6 days, or every 7 days. In some embodiments, the cationic peptide-linked morpholino antisense oligonucleotideis can be administered to the individual for a period of up to one week, two weeks, three, weeks, four weeks, five weeks, six weeks, seven weeks, eight weeks, nine weeks, ten weeks, eleven weeks, twelve weeks, four months, five months, six months, seven months, eight months, nine months, ten months, eleven months, one year, two years, three years, four years, five or more years, or lifetime, inclusive, including periods of time in between these values. In still other embodiments, the cationic peptide-linked morpholino antisense oligonucleotide is administered to the individual in a concentration of any of about 2 mg/kg, 4 mg/kg, 6 mg/kg, 8 mg/kg, 10 mg/kg, 12 mg/kg, 14 mg/kg, 16 mg/kg, 18 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg or more, inclusive, including concentrations in between these values. In one embodiment, said at least one symptom of DM1 is myotonia. In one embodiment, said at least one symptom of DM1 is aggregation of musclebind-like-1 (MBNL-1) protein in ribonuclear foci within myonuclei. In another embodiment, said at least one symptom of DM1 is abnormal splicing of at least one RNA transcript in muscle cells. In some embodiments, the RNA transcript is selected from the group consisting of: Serca-1, m-Titin, Zasp, and ClC-1. In one embodiment, the cationic peptide-linked morpholino antisense oligonucleotide is administered with a pharmaceutically acceptable excipient or carrier, such as any of the pharmaceutically acceptable excipients or carriers described herein. In another embodiment, the individual is human.

In some aspects of any of the methods disclosed herein, said at least one symptom of DM1 is a symptom affecting one or more skeletal muscles. In one embodiment, the symptom is selected from the group consisting of: myotonia, muscle weakness, muscle atrophy, and muscle pain.

In another aspect of any of the methods disclosed herein, said at least one symptom of DM1 is a symptom affecting the cardiovascular system. In one embodiment, the symptom is selected from the group consisting of: cardiogenic syncope and presyncope, cardiac conduction defects, cardiac arrhythmias, hypotension, and congestive heart failure.

In some aspects of any of the methods disclosed herein, said at least one symptom of DM1 is a symptom affecting the respiratory system. In one embodiment, the symptom is selected from the group consisting of: respiratory muscle weakness, aspiration, and sleep apnea.

In another aspect of any of the methods disclosed herein, said at least one symptom of DM1 is a symptom affecting the gastrointestinal system. In one embodiment, the symptom is selected from the group consisting of: chewing and swallowing difficulties, gastroesophageal reflux, abdominal or chest pain (dyspepsia), nausea, vomiting, bloating, bowel pseudo-obstruction, cholestasis, constipation, diarrhea, bowel malabsorption, fecal impaction, megacolon, bowel perforation, dyschezia, and fecal incontinence.

In some aspects of any of the methods disclosed herein, said at least one symptom of DM1 is a symptom affecting the nervous system. In one embodiment, the symptom is selected from the group consisting of: cognitive impairment, excessive daytime sleepiness (hypersomnia), behavioral difficulties, emotional difficulties, socialization difficulties, and peripheral neuropathy.

In another aspect of any of the methods disclosed herein, said at least one symptom of DM1 is a symptom affecting the reproductive and/or endocrine system. In one embodiment, the symptom is selected from the group consisting of: testicular atrophy, female infertility, poor development of secondary sex characteristics, decreased energy, decreased libido, decreased or nonexistent pubic hair, decreased muscle mass, decreased bone mineral density, low serum testosterone, elevated serum luteinizing hormone, elevated serum follicle stimulating hormone, gynecomastia in males, early menopause, insulin resistance, premature male pattern baldness, and elevated estradiol to testosterone ratio levels in males.

In some aspects of any of the methods disclosed herein, said at least one symptom of DM1 is a symptom affecting pregnancy. In one embodiment, the symptom is selected from the group consisting of: spontaneous abortion, stillbirth, prolonged labor and delivery, uterine overdistention, preterm labor, myotonic spasms following the administration of depolarizing agents, respiratory depression following the administration of barbiturates, and post-partum hemorrhage.

In another aspect of any of the methods disclosed herein, said at least one symptom of DM1 is a neonatal complication. In one embodiment, the symptom is selected from the group consisting of: polyhydramnios, umbilical cord prolapse, placental abruption, fetal malposition, hydrops fetalis, and fetal akinesia.

In some aspects of any of the methods disclosed herein, said at least one symptom of DM1 is a symptom affecting the immune system. In one embodiment, the symptom is selected from the group consisting of: hypogammaglobulinemia and increased frequency of pilomatrixoma.

In another aspect of any of the methods disclosed herein, wherein said at least one symptom of DM1 is a symptom affecting the eye or vision. In one embodiment, the symptom is selected from the group consisting of: blurred vision, retinopathy, bilateral blepharoptosis (ptosis), ocular hypotension, and ocular myotonia.

C. Administration of Cationic Peptide-Linked Morpholino Antisense Oligonucleotides In some embodiments, the cationic peptide-linked morpholino antisense oligonucleotide is administered in the form of an injection. The injection can comprise the compound in combination with an aqueous injectable excipient or carrier. Non-limiting examples of suitable aqueous injectable excipients or carriers are well known to persons of ordinary skill in the art, and they, and the methods of formulating the formulations, may be found in such standard references as Alfonso AR: *Remington's Pharmaceutical Sciences,* 17th ed., Mack Publishing Company, Easton Pa., 1985. Suitable aqueous injectable excipients or carriers include water, aqueous saline solution, aqueous dextrose solution, and the like, optionally containing dissolution enhancers such as 10% mannitol or other sugars, 10% glycine, or other amino acids. The composition can be injected subcutaneously, intraperitoneally, or intravenously.

In some embodiments, intravenous administration is used, and it can be continuous intravenous infusion over a period of a few minutes to an hour or more, such as around fifteen minutes. The amount administered may vary widely depending on the type of cationic peptide-linked morpholino antisense oligonucleotide, size of a unit dosage, kind of excipients or carriers, and other factors well known to those of ordinary skill in the art. The cationic peptide-linked morpholino antisense oligonucleotide may comprise, for example, from about 0.001% to about 10% (w/w), from about 0.01% to about 1%, from about 0.1% to about 0.8%, or any range therein, with the remainder comprising the excipient(s) or carrier(s).

For oral administration, the cationic peptide-linked morpholino antisense oligonucleotide can take the form of, for example, tablets or capsules prepared by conventional means with pharmaceutically acceptable excipients or carriers such as binding agents; fillers; lubricants; disintegrants; or wetting agents. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, and coloring as appropriate.

In some embodiments, the cationic peptide-linked morpholino antisense oligonucleotide can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one non-limiting example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

EXAMPLES

Example 1

Intramuscular Injection of Two Different PPMO Conjugates into Tibialis Anterior Corrects aberrant RNA Splicing Large expansions of CUG trinucleotide sequences provide the basis for a toxic RNA gain-of-function that leads to detrimental changes in RNA metabolism. Such a CUG repeat element normally resides in the 3' untranslated region of the protein kinase DMPK, but when expanded it is the genetic lesion of myotonic dystrophy type I (DM1), a hereditary neuromuscular disease. The pathogenic DMPK transcript containing the CUG expansion is retained in ribonuclear foci as part of a complex with RNA binding proteins such as muscleblind-like 1 (MBNL1), resulting in aberrant splicing of numerous RNA transcripts and physiological abnormalities including myotonia.

In this example, condensation synthesis reactions were conducted to generate PPMO conjugates containing a 25 mer CAG sequence-based morpholino (Wheeler et al., 2009, *Science* 325:336-339), CAG25, and a cell-penetrating peptide covalently appended to a spacer moiety located at the 5' end of the morpholino (FIG. 1a). Additionally, to determine the impact of the spacer and peptide modifications upon the bioactivity of PPMO-B and PPMO-K, a series of IM injections into the tibialis anterior (TA) muscle of $HSA^{LR}$ transgenic mice were performed and RNA splicing of Serca-1 was assessed.

Materials and Methods

Conjugation of Cell-Penetrating Peptides to Morpholino oligonucleotides

PPMO conjugates were synthesized as described by Abes et al. with modifications as described hereafter (2006, *J Control Release* 116:304-313). Peptide B (Ac(RXRRBR)$_2$ XB -COOH (SEQ ID NO: 1)) or peptide K (Ac(RXR)$_4$XB-COOH (SEQ ID NO: 2)) (Anaspec, Fremont, CA) was activated in dimethylformamide containing O-(6-Chlorobenzotriazol-1-yl)-N,N,N',N'-tetramethyluronium hexafluorophosphate (HCTU)/diisopropylethylamine (DIEA) at molar ratios of 1:2 per moles of peptide at room temperature (RT). Morpholino CAG25 (5'-AGCAGCA-GCAGCAGCAGCAGCAGCA-3' (SEQ ID NO: 6)) (Gene Tools, Philomath, OR) with a 5' primary amine modification was dissolved in dimethylsulofixide and added to activated peptide B or peptide K at a 1:2-1.5 molar excess of peptide: ASO and the reaction was allowed to proceed for 2 h at RT. The reaction was quenched with water; PPMO conjugates were purified over carboxymethyl sepharose (GE Healthcare, Piscataway, NJ) and eluted in 2M guanidine-HCl, 1M NaCl, pH 7.5, 20% acetonitrile. The eluate was dialyzed against several buffer exchanges of 0.1mM NaHCO$_3$ in a dialysis cassette with molecular weight cut-off of 3,000Da. The dialyzed PPMO was quantified by spectrophotometric absorbance in 0.1N HCl at 265nm, frozen, and lyophilized.

$HSA^{LR}$ rederivation and genotyping

Re-derived hemizygous $HSA^{LR}$ mice were produced by impregnating FVB/n wild-type female mice with sperm collected from homozygous $HSA^{LR}$ line 20b males. Male and female hemizygous mice were mated together to generate homozygous offspring. A quantitative multiplex real-time PCR assay was used to determine the zygosity status of mice; this assay detects human skeletal actin (ACTA1) and Gapdh as an internal control in the same well. The following primer-probe set (Life Technologies, Grand Island, NY) was used to detect ACTA1 genomic DNA: Forward: 5'-CCAC-CGCAAATGCTTCTAGAC (SEQ ID NO: 10), Reverse: 5'-CCCCCCCATTGAGAAGATTC (SEQ ID NO: 11), Probe: 5'-CTCCACCTCCAGCACGCGACTTCT (SEQ ID NO: 12). A proprietary sequence primer-probe set (Life Technologies, Grand Island, NY) was used to detect Gapdh genomic DNA. Homozygous mice were subsequently backcrossed to wild-type FVB/n to confirm homozygosity status. Confirmed male and female homozygous mice were then mated together to maintain a homozygous colony on an FVB/n background strain.

Real-Time PCR of $HSA^{LR}$ Transgene mRNA

Total RNA was purified from TA, gastrocnemius, and quadriceps using the RNeasy Lipid Tissue Mini Kit (Qiagen, Valencia, CA) according to the manufacturer's instructions. Quantitative real-time PCR was used to determine the mRNA level of the $HSA^{LR}$ transgene; 18S RNA level was used as a normalization factor. The 18S RNA level was determined using a primer-probe set of proprietary sequences (Life Technologies, Grand Island, N.Y.). The same primer-probe set used to detect ACTA1 genomic DNA was used to detect ACTA1 mRNA Intramuscular TA Injections The Genzyme Institutional Animal Care and Use Committee approved all animal studies. The TA of isoflurane-anesthetized mice was injected and subjected to electroporation as described Wheeler et al., 2007, *J Clin Invest* 117:3952-3957). One TA was injected with 20µg (1 µg/µL) of CAG25, GAC25 (5'-ACGACGACGACGACGACGAC-GACGA-3' (SEQ ID NO: 13) (Gene Tools, Philomath, OR), or PPMO (in PPMO-B and PPMO-K injections, 20 µg ASO equivalent mass was injected, taking into account the mass of the peptide) whereas the contralateral TA was injected with 20 µL phosphate-buffered saline (saline).

Results

Two PPMO conjugates were synthesized containing either peptide B or peptide K and will be referred to as PPMO-B and PPMO-K, respectively.

IM injections of CAG25 into TA corrected Serca-1 splicing whereas the contralateral TA that received an injection of saline retained the abnormal pattern of Serca-1 splicing (FIG. 1b). A control morpholino of GAC sequence, GAC25, did not correct Serca-1 splicing as anticipated.

Importantly, these results indicate that IM injections of both PPMO-B and PPMO-K corrected Serca-1 splicing indicating that the peptide and spacer covalent modifications at the 5' end of the morpholino do not compromise the ability of CAG25 to interact with its target and neutralize the toxic effects of CUG RNA (FIG. 1b).

Example 2

Repeated IV Injections of PPMO-B and PPMO-K Effectively Ameliorate Spliceopathy in vivo Having confirmed that modification of CAG25 with peptide B or K did not abrogate its bioactivity, this example evaluates whether PPMO-B and PPMO-K could modulate the effects of toxic RNA in $HSA^{LR}$ mice using an IV dosing regimen.

Materials and Methods

Systemic Delivery Studies in $HSA^{LR}$

CAG25, PPMO-B, and PPMO-K were dissolved in saline and administered to male and female $HSA^{LR}$ homozygous mice at a dose of 30 mg/kg bodyweight by tail vein IV injection once a week for six weeks. Blood was collected by retro-orbital bleed 24 h following the last dose. Approximately one week following the final dose, mice were evaluated for the presence of myotonia as described in Electromyography procedures. Mice were then killed; muscle sections were frozen in liquid N$_2$ for RNA analyses or embedded in OCT medium and frozen in cooled isopentane for immunofluorescence and FISH analyses.

RT-PCR Analysis of Alternative Splicing

RT-PCR was carried out using the SuperScript III One-Step RT-PCR System with Platinum Taq DNA Polymerase (Life Technologies, Grand Island, N.Y.) with gene-specific primers used for cDNA synthesis and PCR amplification. The primer sequences for Serca-1, ZASP, m-Titin and C1C-1 have been described previously (Wheeler et al., 2007, *J Clin Invest* 117:3952-3957; Lin et al., 2006, *Hum Mol Genet* 15:2087-2097). PCR products were electrophoresed on agarose gels, stained with SybrGreen I Nucleic Acid Gel Stain (Life Technologies, Grand Island, N.Y.) and imaged using a Fujifilm LAS-3000 Intelligent Dark Box.
Results $HSA^{LR}$ mice were subjected to six weekly IV injections of CAG25, PPMO-B and PPMO-K at a dose of 30mg/kg. $HSA^{LR}$ mice tolerated this dose well and exhibited no overt signs of toxicity during CAG25 and PPMO administration or throughout the study period. Additionally, these treatments did not affect liver transaminases (ALT, AST) or markers of kidney function (creatinine, BUN) (data not shown).

Figure 2:
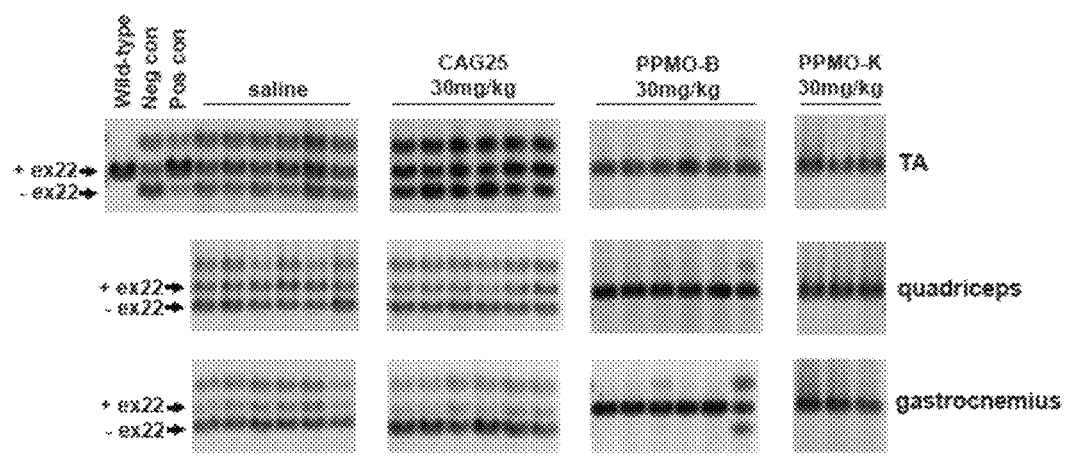
FIG. 2 depicts repeated IV injections of PPMO-B or PPMO-K correct Serca-1 splicing. HSA$^{LR}$ mice were injected with saline, CAG25, PPMO-B, or PPMO-K weekly for six weeks. The indicated muscle groups were collected from mice approximately one week following the last dose. Total RNA was purified, and Serca-1 was amplified to detect differentially-spliced isoforms. RNA from the TA of a FVB/n wild-type mouse serves as a control as in FIG.1. Serca-1 splicing in RNA purified from the TA of HSA$^{LR}$ mice injected with GAC25 or CAG25 as in FIG. 1 serves as a negative control (neg con) and a positive control (pos con), respectively.

Splicing analysis was conducted on several muscle groups including the TA, quadriceps and gastrocnemius. As shown in FIG. 2, both PPMO-B and PPMO-K dramatically corrected Serca-1 splicing and restored the pattern of splicing to that observed in wild-type mice. Serca-1 splicing correction occurred in all muscles examined including TA, quadriceps, and gastrocnemius. One mouse treated with PPMO-B showed partial splicing correction in quadriceps and gastrocnemius. In contrast to PPMO-B and PPMO-K, intravenous injections of unmodified CAG25 led to no improvements in Serca-1 splicing in any muscle groups examined (FIG. 2). This is consistent with other studies showing inferior biodistribution of bare morpholinos to muscle (Sazani, et al., 2002, Nat Biotechnol 20:1228-1233).

Figure 3:
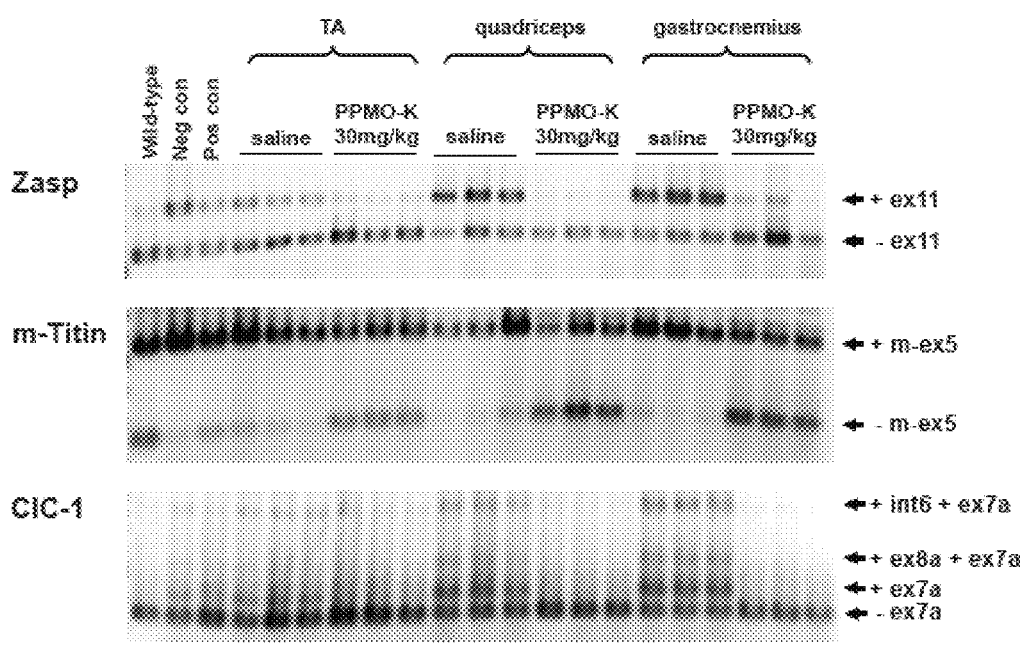
FIG. 3 depicts correction of abnormal splicing of ZASP, m-Titin, and C1C-1 in HSA$^{LR}$ mice dosed with repeated IV injections of PPMO-K. HSA$^{LR}$ mice were injected with saline or PPMO-K once a week for six weeks. The indicated muscle groups were collected from mice, total RNA was purified, and ZASP, m-Titin, and C1C-1 were amplified to detect differentially-spliced isoforms containing the indicated exon (ex) and intron (int) configurations. RNA from the TA of a FVB/n wild-type mouse serves as a non-disease control. Positive and negative controls were generated with RNA as in FIG. 2 with PCR amplification for ZASP, m-Titin, and C1C-1.

Additional transcripts dependent upon MBNL1 for proper splicing include m-Titin, Zasp and C1C-1.8,24 As shown in FIG. 3, systemic delivery of PPMO-K led to robust corrections in RNA splicing of m-Titin, Zasp and C1C-1 in TA, quadriceps, and gastrocnemius. HSALR mice treated with IV injections of PPMO-B likewise demonstrated corrections in alternative splicing for these transcripts (data not shown).

These results suggest that systemically delivered PPMO-B and PPMO-K are able to penetrate into skeletal muscle, enter into muscle myonuclei, hybridize with poly (CUG) RNA, and liberate an amount of sequestered MBNL1 protein sufficient to restore correct MBNL1-regulated RNA splicing.

Example 3

Figure 4:
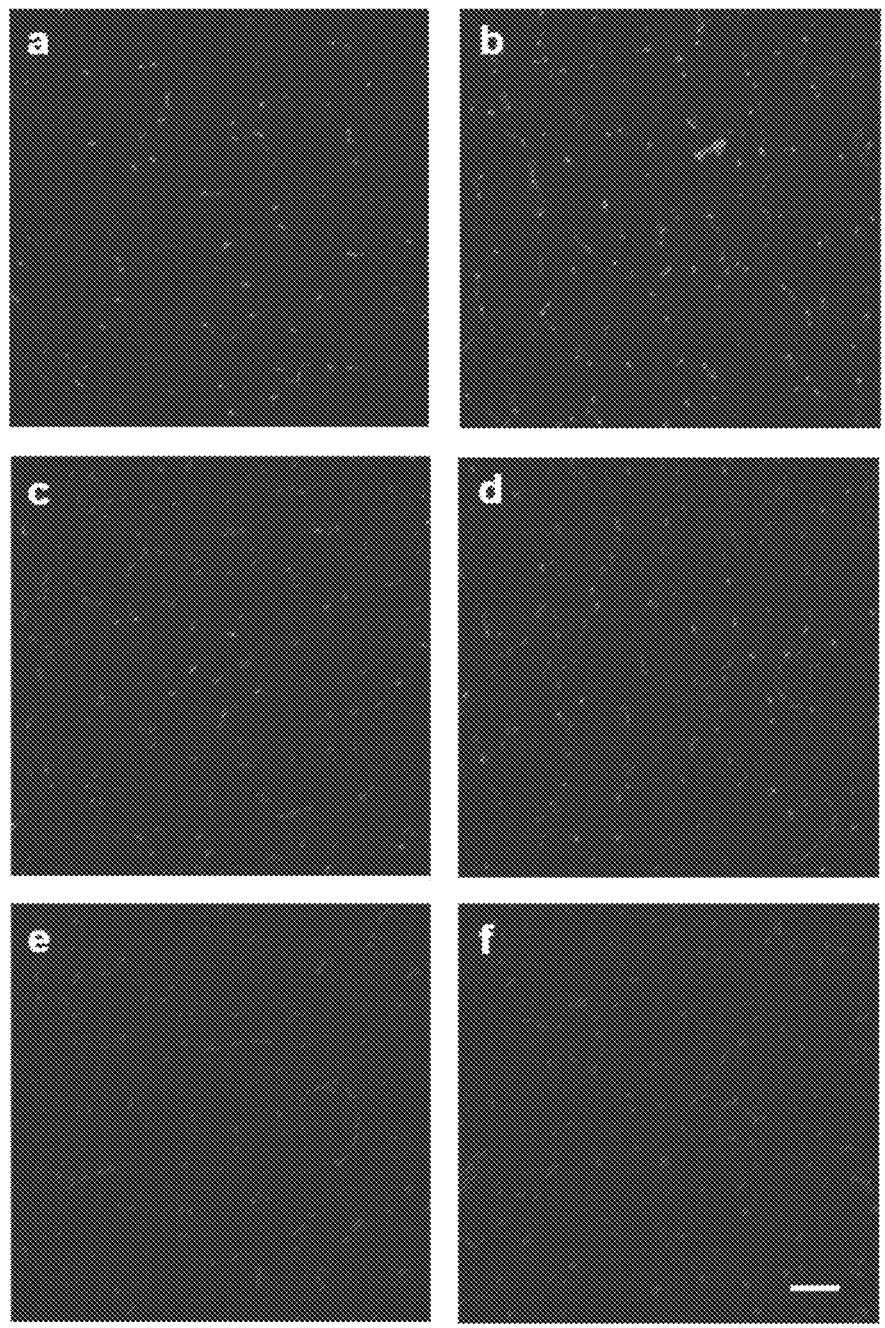
FIG. 4 depicts systemic delivery of PPMO-K reduces the frequency and intensity of CUG RNA foci in quadriceps of HSA$^{LR}$ mice. FISH analysis was conducted upon frozen quadriceps sections as described (Mankodi et al., 2001, *Hum Mol Genet* 10:2165-2170) using a 2'-O-methyl-modified RNA probe (5'-GCAGCAGCAGCAGCAGCAGC-3' (SEQ ID NO: 7) labeled at the 5' end with AlexaFluor 555 and visualized via confocal microscopy. (a,b) HSA$^{LR}$ mice treated with six weekly IV injections of saline show abundant CUG RNA foci in muscle nuclei labeled with DAPI. (c,d) HSA$^{LR}$ treated with six weekly IV injections of PPMO-K (30mg/kg) show a reduction in the number and intensity of CUG RNA foci. (e,f) Wild-type FVB/n muscle does not contain detectable foci. Scale bar =50 μm.
Figure 5:
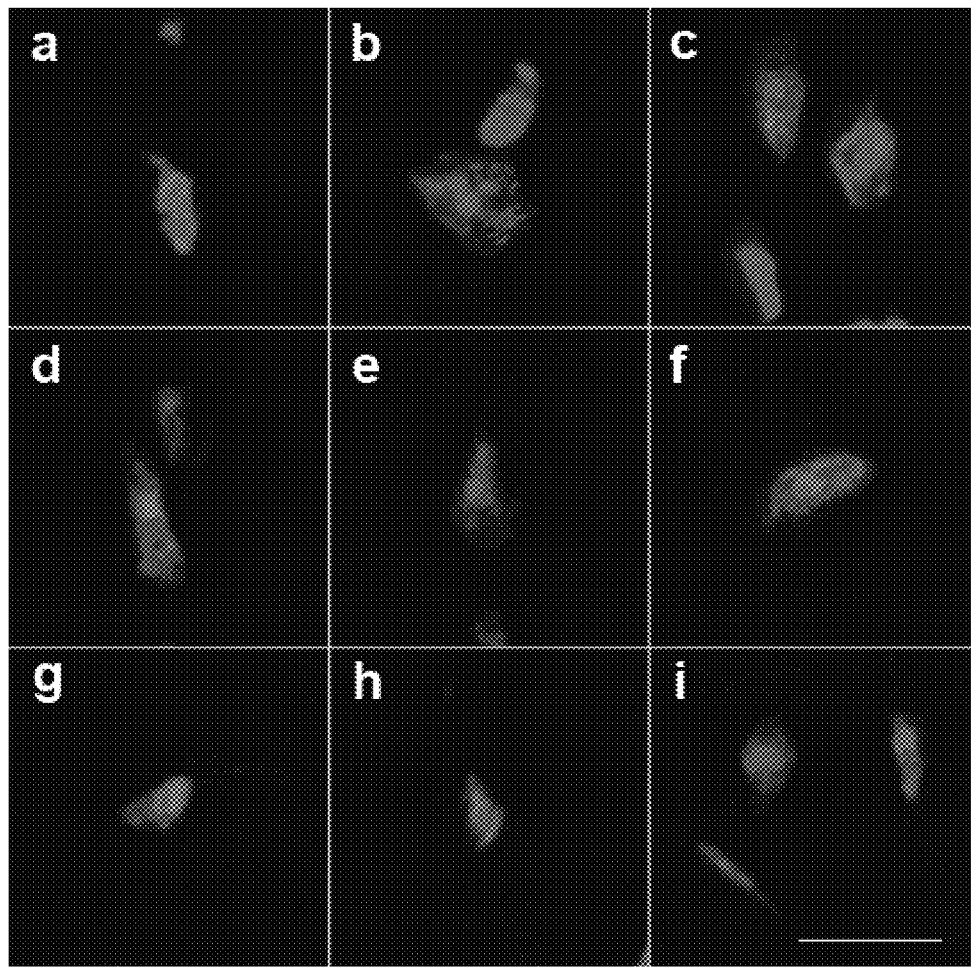
FIG. 5 depicts immunofluorescence microscopy demonstrates nuclear redistribution of MBNL1 protein in PPMO-K-treated mice Immunofluorescence staining of MBNL1 proteins in sections of quadriceps muscle and confocal microscopy was carried out as described in the Materials and Methods. (a-c) Muscle sections from saline-treated HSA$^{LR}$ mice show punctate localization of MBNL1 in the nucleus. (d-f) Muscle sections from PPMO-K-treated HSA$^{LR}$ mice show diffuse nuclear staining of MBNL1. (g-i) Muscle sections from a wild-type FVB/n mouse show diffuse nuclear staining of MBNL1. Scale bar=10 μm.

PPMO-K Disrupts CUG Nuclear Inclusion Complexes in Skeletal Muscle and Results in a Redistribution of MBNL1 Protein In order to determine the fate of ribonuclear foci in mice treated with PPMO-K, this example demonstrates fluorescence in situ hybridization (FISH) to detect CUG ribonuclear inclusions in muscle.
Materials and Methods Frozen sections of quadriceps muscle 6 μm thick were processed to detect localization of MBNL1 protein via immunofluorescence as described (Lin et al., 2006, Hum Mol Genet 15:2087-2097) with the following modifications: the polyclonal antibody A2764 was used at a concentration of 1:5000 followed by incubation with Alex-568-labeled goat-anti-rabbit polyclonal secondary antibody at a concentration of 1:500. Samples were imaged using a LSM510 META laser scanning confocal microscope configured for imaging DAPI and Alexa Fluor-568 sequentially. Examination was conducted using a 100x/NA1.45 Plan-Fluar oil immersion objective with 4x zoom.
Results In PPMO-K-treated $HSA^{LR}$ mice, a reduction in the number and intensity of CUG foci was observed (FIG. 4). However, because the oligonucleotide sequence of PPMO-K and the probe utilized in the FISH procedure consist of the same (CAG)n sequence, it is not possible to determine whether the effects upon RNA foci are due to disruption of the foci by PPMO-K or binding competition between PPMO-K and the FISH probe. As a more direct, unequivocal means to ascertain the effect of PPMO-K upon foci, we performed immunofluorescence labeling of MBNL1, which is sequestered in CUG RNA foci and shows punctate staining in the nucleus of $HSA^{LR}$ mice (FIG. 5a-c). As shown in FIG. 5d-f, PPMO-K led to a re-distribution of MBNL1 protein and resulted in a more diffuse localization within the nucleoplasm as is observed in wild-type mice (FIG. 5g-i).

Taken together, the immunostaining and FISH data in this example suggest that PPMO-K interacts with CUG RNA in a competitive manner thereby leading to a re-distribution of MBNL1 protein within myonuclei. The liberation of MBNL1 in skeletal muscle foci is consistent with the correction of RNA splicing observed in PPMO-K-treated mice.

Example 4

Myotonia is Corrected in $HSA^{LR}$ Mice Subjected to IV Injections of PPMO-K

Figure 6:
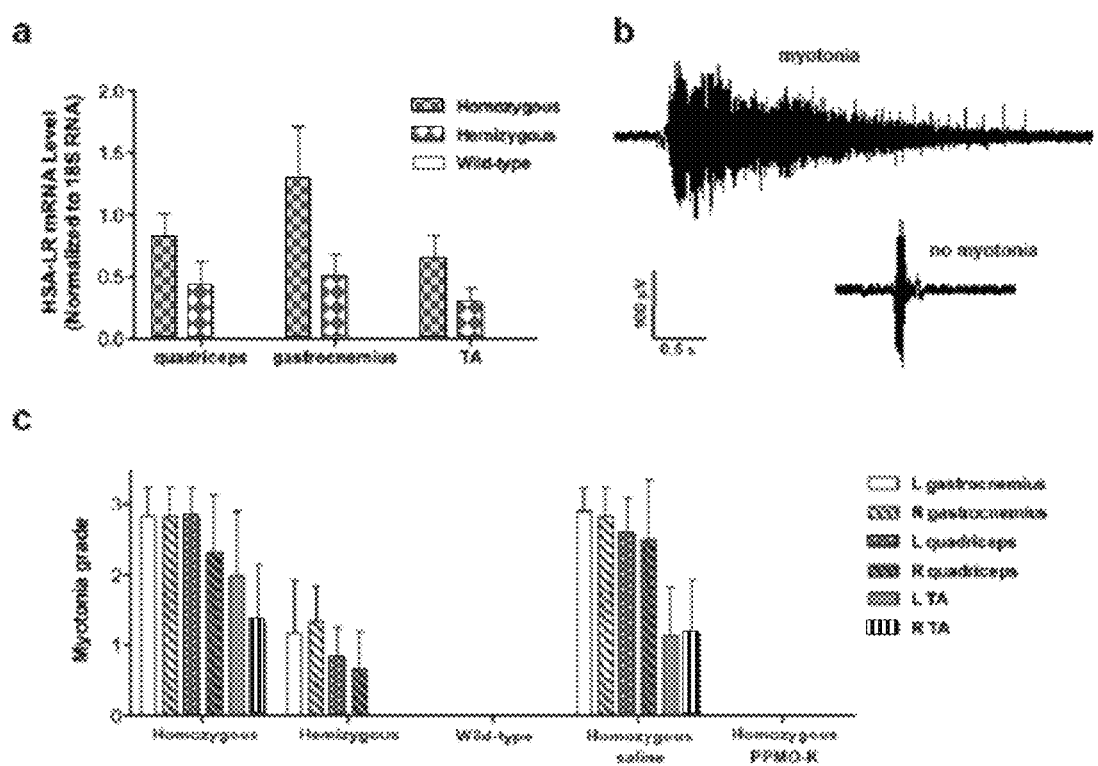
FIG. 6 depicts myotonia is corrected in HSA$^{LR}$ mice dosed with repeated IV injections of PPMO-K (a) HSA$^{LR}$ transgene mRNA levels normalized to 18S RNA in TA, gastrocnemius, and quadriceps of homozygous HSA$^{LR}$, hemizygous HSA$^{LR}$, and wild-type FVB/n mice. Data are presented as the mean+SD, n=6 mice per group. (b) Tracings of EMG recordings in gastrocnemius muscle of HSA$^{LR}$ (myotonia) or wild-type FVB/n mice (no myotonia). Myotonia is detected in HSA$^{LR}$ mice but not wild-type mice. (c) EMG analysis was conducted on untreated homozygous HSA$^{LR}$, hemizygous HSA$^{LR}$, and wild-type mice. EMG was also conducted on homozygous HSA$^{LR}$ mice treated with six weekly injections of saline or PPMO-K. Each muscle was analyzed 10 times to generate a myotonia grade as described in the Materials and Methods. Data are presented as the mean grade+SD for each muscle group tested, n=3-8 mice per group.

The correction of C1C-1 RNA splicing by PPMO-B and PPMO-K suggest that restoration of chloride channel function may result in alterations in the severity of myotonia that is typically observed in $HSA^{LR}$ mice. To test this possibility, myotonia in saline-treated and PPMO-K-treated $HSA^{LR}$ mice were evaluated in this example by EMG.
Materials and Methods EMG was performed upon isoflurane-anesthetized mice with EMG samplings taken in TA, gastrocnemius, and quadriceps using two 29 gauge needle electrodes. After insertion of both needles, the muscle was gently manipulated with forceps at the site of needle entry. Myotonia was graded via the following criteria: 0 indicates no myotonic discharges detected; 1 indicates less than 50% of muscle manipulations resulted in a myotonic discharge; 2 indicates 50% to 80% of muscle manipulations resulted in a myotonic discharge; 3 indicates that 90% to 100% of muscle manipulations resulted in a myotonic discharge.
Results Myotonia was first assessed in wild-type FVB/n, hemizygous and homozygous $HSA^{LR}$ mice. Hemizygous mice contain approximately 50% of the level of $HSA^{LR}$ mRNA in skeletal muscle vs. homozygous mice (FIG. 6a). A reduction in the occurrence of myotonia in hemizygous mice relative to homozygous mice and no myotonia in wild-type mice was observed (FIG. 6c) as expected. A tracing of a typical myotonic discharge that we detected in homozygous $HSA^{LR}$ mice is shown in FIG. 6b. As shown in FIG. 6b, no myotonia was detected in $HSA^{LR}$ mice treated with PPMO-K, consistent with the corrections in C1C-1 alternative splicing that occurred in these mice (FIG. 3).

CONCLUSIONS

The experiments conducted herein show that the addition of a cell penetrating peptide to a CAG sequence morpholino permits sufficient uptake of PPMO systemically into skeletal muscle to neutralize the toxic effects of an elongated CUG repeat. Near complete resolution of splicing defects, release of MBNL1 from RNA foci, and elimination of myotonia was observed.

The finding that systemic delivery of a morpholino oligonucleotide can modulate DM1-like pathology in vivo is multi-fold in significance: first, 5' covalent modification of a CAG-based morpholino does not detract from interaction with target CUG RNA; second, the biodistribution that is rendered achievable by arginine-rich cell-penetrating peptides is sufficient to confer corrections in biochemical and physiological aspects of DM1 pathology; and thirdly, the test agent administered in the studies presented here in the HSA$^{LR}$ model of DM1 is the same therapeutic candidate that could be evaluated for safe use in human DM1 patients.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating or preventing myotonic dystrophy type 1 (DM1) in an individual in need thereof comprising: systemically administering to the individual a therapeutically effective amount of a cationic peptide-linked morpholino antisense oligonucleotide comprising: (a) a morpholino antisense oligonucleotide sequence complementary to at least 3 polyCUG repeat sequences in a 3' untranslated region (UTR) of a dystrophia myotonica protein kinase (DMPK) RNA transcript target; and (b) a spacer moiety linking the morpholino antisense oligonucleotide and a cationic peptide, the space moiety comprising

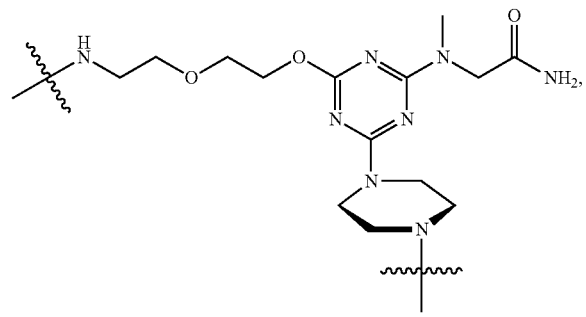

wherein administration of the cationic peptide-linked morpholino antisense oligonucleotide relieves at least one symptom of DM1 in at least two muscles.

2. The method of claim 1, wherein the cationic peptide is 8-30 amino acid residues in length and comprises one or more subsequences selected from the group consisting of RXR, RX, RB, and RBR, wherein R is arginine, B is β-alanine, and each X is independently —NH—$(CHR^1)_n$—C(O)—, wherein n is 4-6 and each $R^1$ is independently H or methyl such that at most two $R^1$s are methyl.

3. The method of claim 1, wherein the cationic peptide-linked morpholino antisense oligonucleotide comprises the sequence 5'-$(AGC)_n$-3'(SEQ ID NO:3), 5'-$(GCA)_n$-3'(SEQ ID NO:4), or 5'-$(CAG)_n$-3'(SEQ ID NO:5), wherein n is any of about 5-25.

4. The method of claim 3, wherein the cationic peptide-linked morpholino antisense oligonucleotide further comprises 1 to 2 additional morpholino nucleotides on the 5' and/or the 3' end of the oligonucleotide.

5. The method of claim 3, wherein the cationic peptide-linked morpholino antisense oligonucleotide comprises the sequence: 5'-AGCAGCAGCAGCAGCAGCAGCAGCA-3' (SEQ ID NO:6).

6. The method of claim 5, wherein the cationic peptide-linked morpholino antisense oligonucleotide further comprises a 5' amine modification.

7. The method of claim 1, wherein the cationic peptide-linked morpholino antisense oligonucleotide is a phosphorodiamidate cationic peptide-linked morpholino antisense oligonucleotide.

8. The method of claim 1, wherein the cationic peptide is separated from the morpholino antisense oligonucleotide by the spacer moiety linked at the 5' end of the morpholino antisense oligonucleotide.

9. The method of claim 1, wherein the muscles are skeletal muscles, smooth muscles, and/or cardiac muscle.

10. The method of claim 1, wherein the cationic peptide-linked morpholino antisense oligonucleotide penetrates into cells of the tibialis anterior muscle, the quadriceps muscle, and/or the gastrocnemius muscle.

11. The method of claim 1, wherein said at least one symptom of DM1 is myotonia.

12. The method of claim 1, wherein said at least one symptom of DM1 is aggregation of musclebind-like-1 (MBNL-1) protein in ribonuclear foci within myonuclei.

13. The method of claim 1, wherein said at least one symptom of DM1 is abnormal splicing of at least one RNA transcript in muscle cells.

14. The method of claim 13, wherein said at least one RNA transcript is selected from the group consisting of: Serca-1, m-Titin, Zasp, and CIC-1.

15. The method of claim 1, wherein systemic administration of the cationic peptide-linked morpholino antisense oligonucleotide is performed intravenously, intraperitoneally, or subcutaneously.

16. The method of claim 1, wherein the cationic peptide-linked morpholino antisense oligonucleotide is administered to the individual weekly.

17. The method of claim 1, wherein the cationic peptide-linked morpholino antisense oligonucleotide is administered to the individual for at least one week.

18. The method of claim 1, wherein the cationic peptide-linked morpholino antisense oligonucleotide is administered with a pharmaceutically acceptable excipient.

19. The method of claim 1, wherein the individual is a human.

20. A method for treating or preventing myotonic dystrophy type 1(DM1) in an individual in need thereof comprising: systemically administering to the individual a therapeutically effective amount of a cationic peptide-linked morpholino antisense oligonucleotide comprising: (a) morpholino antisense oligonucleotide sequence complementary to at least 3polyCUG repeat sequences in a 3' untranslated region (UTR) of a dystrophia myotonica protein kinase (DMPK) RNA transcript target; (b) a spacer moiety linking the morpholino antisense oligonucleotide and a cationic peptide, the space moiety comprising

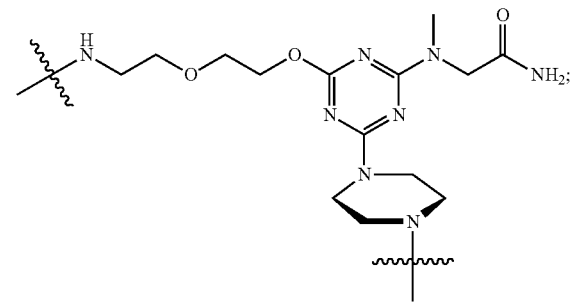

and
(c) the, cationic peptide comprising the amino acid sequence Ac(RXRRBR)$_2$XB-(SEQ ID NO:1), wherein Ac is acetyl, R is arginine, B is β-alanine, and each X is independently —NH—$(CHR^1)_n$—,C(O)—, wherein n is 4-6 and each $R^1$ is independently H or methyl such that at most two $R^1$s are methyl, and wherein administration of the cationic peptide-linked rnorpholino antisense oligonucleotide relieves at least one symptom of DM1 in at least two muscles.

21. A method for treating or preventing myotonic dystrophy type 1(DM1) in an individual in need thereof comprising: systemically administering to the individual a therapeutically effective amount of a cationic peptide-linked morpholino antisense oligonucleotide comprising: (a) a morpholino antisense oligonucleotide sequence complementary to at least 3polyCUG repeat sequences in a 3' untranslated region (UTR) of a dystrophia myotonica protein kinase (DMPK) RNA transcript target: (b) a spacer moiety linking the morpholino antisense oligonucleotide and a cationic peptide, the space moiety comprising

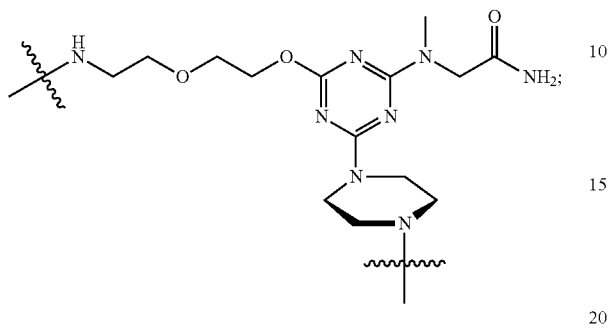

and (c) the, cationic peptide comprising the amino acid sequence Ac(RXR)$_4$XB-(SEQ ID NO:2), wherein Ac is acetyl, R is arginine, B is β-alanine, and each X is independently —NH—(CHR$^1$)$_n$—C(O)—, wherein n is 4-6 and each R$^1$ is independently H or methyl such that at most two R$^1$s are methyl, and wherein administration of the cationic peptide-linked morpholino antisense oligonucleotide relieves at least one symptom of DM1 in at least two muscles.

* * * * *

UNITED STATES PATENT AND TRADEMARK OFFICE
CERTIFICATE OF CORRECTION

PATENT NO. : 10,111,962 B2
APPLICATION NO. : 14/431115
DATED : October 30, 2018
INVENTOR(S) : Leger et al.

Page 1 of 1

It is certified that error appears in the above-identified patent and that said Letters Patent is hereby corrected as shown below:

In the Claims

In Claim 3, Column 39, Line 40: please replace "5'-(AGC)$_n$-3'(SEQ ID NO:3),5'-(GCA)$_n$-3'(SEQ ID NO:4), or 5'-(CAG)$_n$-3'(SEQ ID NO:5)" with --5'-(AGC)$_n$-3' (SEQ ID NO:3), 5'-(GCA)$_n$-3' (SEQ ID NO:4), or 5'-(CAG)$_n$-3' (SEQ ID NO:5)--;

In Claim 20, Column 40, Line 28: please replace "type 1(DM1)" with --type 1 (DM1)--;

In Claim 20, Column 40, Line 33: please replace "3polyCUG" with --3 polyCUG--;

In Claim 20, Column 40, Line 54: please replace "the, cationic" with --the cationic--;

In Claim 20, Column 40, Line 57: please replace "-NH-(CHR$^1$)$_n$-,C(O)-" with -- -NH-(CHR$^1$)$_n$-C(O)- --;

In Claim 21, Column 40, Line 64: please replace "type 1(DM1)" with --type 1 (DM1)--;

In Claim 21, Column 41, Line 2: please replace "3polyCUG" with --3 polyCUG--; and In Claim 21, Column 41, Line 23: please replace "the, cationic" with --the cationic--.

Signed and Sealed this
Twenty-ninth Day of September, 2020

Andrei Iancu
*Director of the United States Patent and Trademark Office*